(12) United States Patent
Ohlrogge et al.

(10) Patent No.: US 6,218,600 B1
(45) Date of Patent: Apr. 17, 2001

(54) STRUCTURE AND EXPRESSION OF THE BIOTIN CARBOXYLASE SUBUNIT OF HETEROMERIC ACETYL-COA CARBOXYLASE

(75) Inventors: John B. Ohlrogge, Okemos; Basil Shorrosh, Lansing, both of MI (US); Keith Roesler, Urbandale, IA (US); David Shintani, Laingsburg, MI (US); Chris Somerville, Portola Valley, CA (US)

(73) Assignee: Board of Trustees Operating Michigan State University, East Lansing, MI (US)

( * ) Notice: Subject to any disclaimer, the term of this patent is extended or adjusted under 35 U.S.C. 154(b) by 0 days.

(21) Appl. No.: 08/662,344

(22) Filed: Jun. 12, 1996

(51) Int. Cl.[7] .............................. A01H 5/00; A01H 5/10; C12N 15/82

(52) U.S. Cl. ...................... 800/298; 536/23.6; 435/320.1

(58) Field of Search .................................... 800/205, 250, 800/298, 278, 281; 435/69.1, 172.3, 320.1, 418, 419; 536/23.6

(56) References Cited

U.S. PATENT DOCUMENTS 5,498,544   3/1996   Gegenbach et al. .............. 435/320.1

OTHER PUBLICATIONS

Al–Feel, W. et al., "Cloning of the Yeast FAS3 Gene and Primary Structure of Yeast Acetyl–CoA Carboxylase," *PNAS (USA)* 89:4534–4538 (1992).

Alban, C. et al., Localization and Characterization of Two structurally Different Forms of Acetyl–CoA Carboxylase in Young Pea Leaves, of which One is Sensitive to ARyloxyphenoxypropionate Herbicides, *Biochem. J.* 300:557–565 (1994).

Alix, J–H. et al., "Laboratory Methods a Rapid Procedure for Cloning Genes from λ Libraries by Complementation of *E. Coli* Defective Mutants: Application of the fabE Region of the *E. coli* Chromosome," *DNA* 8:779–789 (1989).

Ashton, A.R. et al., "Molecular Cloning of Two Different cDNAs for Maize Acetyl CoA Carboxylase," *Plant Mol. Biol.* 24:35–49 (1994).

Baldet et al., "Characterization of Biotin and 3–Methylcrotonyl–Coenzyme a Carboxylase in Higher Plant Mitochondria," *Plant Physiol.* 99:450–455 (1992).

Baldet, P. et al., "Localization of Free and Bound Biotin in Cells from Green Pea Leaves," *Arch. Biochem. Biophys.* 303:67–73 (1993).

Beremand et al., "Synthesis, Cloning, and Expression in *Escherichia coli* of a Spinach Acyl Carrier Protein–I Gene," *Arch. Bioch. Biophys.* 256:90–100 (1987).

Borchert, S. et al., "Specific Transport of Inorganic Phosphate, Glucose 6–Phoshate, Dihydroxyacetone Phosphate and 3–Phosphoglycerate into Amyloplasts from Pea Roots," *FEBS Letters* 253:183–186 (1989).

Bradfird, M.M., "A Rapid and Sensitive Method for the Quantitation of Microgram Quantities of Protein Utilizing the Principle of Protein–Dye Binding," *Anal. Biochem.* 72:248–254 (1976).

Cline, K. et al., "Precursors to Two Nuclear–Encoded Chloroplast Proteins Bind to the Outer Envelope Membrane before Being Imported into Chloroplasts," *J. Biol. Chem.* 260:3691–3695.

Duval et al., "Developmental Patterns of Free and Protein–Bound Biotin During Maturation and Germination of Seed of *Pisum sativum*: Characterization of a Novel Seed–Specific Biotinylated Protein," *Biochem J.* 299:141–150 (1994).

Duval et al., "The Major Biotinyl Protein from *Pisum sativum* Seeds Covalently Binds Biotin at a Novel Site," *Plant Mol. Biol.* 26:265–273 (1994).

Ebel, J. et al., "Phytoalexin Synthesis in Soybean Cells: Elicitor Induction of Phenylalanine Ammonia–Lyase and Chalcone Synthase mRNAs and Correlation with Phytoalexin Accumulation," *Arch. Biophys.* 232:240–248 (1984).

Ebel, J. et al., "Enzymes of Flavone and Flavonol Glycoside Biosynthesis. Coordinated and Selective Induction in Cell–Suspension Cultures of *Petroselinum Hortense*," *Eur. J. Biochem.* 75:201–209 (1977).

Egli, M.A. et al., "Characterization of Maize Acetyl–Coenzyme A Carboxylase," *Plant Physiol.* 101:499–506 (1993).

Elborough, K.M. et al., "Studies on Wheat Acetyl CoA Carboxylase and the Cloning of a Partial cDNA," *Plant Mol. Biol.* 24:21–34 (1994).

Gornicki, P. et al., "Genes for Two Subunits of Acetyl Coenzyme a Carboxylase of *Anabaena* sp. Strain PCC 7120: Biotin Carboxylase and Biotin Carboxyl Carrier Protein," *J. Bacteriology* 175:5268–5272 (1993).

Gornicki, P. et al., Wheat Acetyl–Coenzyme A Carboxylase: CDNA and Protein Strucuture,: *PNAS (USA)* 91:6860–6864 (1994).

Greenwood, J.S. et al., "Seed Development in *Ricinus Communis* (castor bean). I. Descriptive Morphology," *Can. J. Bot.* 60:1751–1760 (1982).

(List continued on next page.)

Primary Examiner—Elizabeth F. McElwain
(74) Attorney, Agent, or Firm—Lahive & Cockfield, LLP

(57) ABSTRACT

The gene encoding a biotin carboxylase subunit of heteromeric ACCase has been isolated and sequenced. The cDNA sequence and deduced amino acid sequence is set forth in FIG. 1 and has been accorded GenBank Accession No. L38260. By controlling expression of the gene of the present invention, carboxylation of acetyl-CoA to produce malonyl-CoA may be controlled. Thus, by introducing constructs of the gene of the present invention in sense or anti-sense orientation, carboxylation of acetyl-CoA to produce malonyl-CoA may be increased or decreased. Consequently, fatty acid synthesis in plants and seeds which depends on malonyl-CoA in the plastid may also be controlled.

6 Claims, 11 Drawing Sheets

OTHER PUBLICATIONS

Ha, J. et al., "Inhibition of Fatty Acid Synthesis by Expression of an Acetyl–CoA Carboxylase–Specific Ribozyme Gene," *PNAS (USA)* 91:9951–9955 (1994).

Ha, J. et al., "Cloning of Human Acetyl–CoA Carboxylase cDNA," *Eur. J. Biochem.* 219:297–306 (1994).

Harwood, J.L., "Fatty Acid Metabolism," *Annu. Rev. Plant Physiol. Plant Mol. Biol.* 39:101–138 (1988).

Holmes, D.S. et al., "A Rapid Boiling Method for the Preparation of Baterial Plasmids," *Anal. Biochem.* 114:193–197 (1981).

Kolattukudy, P.E. et al., "Chain Elongation of Fatty Acids by Cell–Free Extracts of Epidermis from Pea Leaves (*Pisum Sativum*)," *Biochem. Biophys. Res. Comm.* 46:801–807 (1972).

Kondo, H. et al., "Acetyl–CoA Carboxylase from *Escherichia coli*: Gene Organization and Nucleotide Sequence of the Biotin Carboxylase Subunit," *PNAS (USA)* 88:9730–9733 (1989).

Konishi, T. et al., "Compartmentalization of Two Forms of Acetyl–CoA Carboxylase in Plants and the Origin of Thier Tolerance Toward Herbicides," *PNAS (USA)* 91:3598–3601 (1994).

Laemmli, U.K., "Cleavage of Structural Proteins During the Assembly of the Head of Bacteriophage T4," *Nature* 227:680–685 (1970).

Li, S–J. et al., "The Gene Encoding the Biotin Carboxylase Subunit of *Escherichia coli* Acetyl–CoA Carboxylase," *J. Biol. Chem.* 267:855–863 (1992a).

Li, S–J. et al., "The Genes Encoding the Two Carboxyltransferase Subunits of *Escherichia coli* Acetyl–CoA Carboxylase," *J. Biol. Chem.* 267:16841–16847 (1992b).

Lopez–Casillas, F. et al., "Structure of the Coding Sequence and Primary Amino Acid Sequence of Acetyl–Coenzyme A Carboxylase," *PNAS (USA)* 85:5784–5788 (1988).

Miernyk, J.A., "The Isolation and Characterization of Nongreen Plants," *Methods of Plant Analys* pp. 259–295 Edited by HF Linskens and J.F. Jackson. Springer–Verlag Berlin Heidelberg (1985).

Mukherjee, K.D. et al., "Changes in Fatty Acid Compositions of Lipid Classes in Developing Mustard Seed," *Phytochem.* 23:349–352 (1984).

Norton and Harris, "Compositional Changes in Developing Rape Seed (*Brassica napus* L.)," *Planta.* 123:163–174 (1975).

Page, R.A. et al., Acetyl–CoA Carboxylase Exerts Strong Flux Control Over Lipid Synthesis in Plants, *Biochem. Biophys.* 1210:369–372 (1994).

Poirier Y. et al., "Polyhydroxybutyrate, a Biodegradable Thermoplastic, Producedin Transgenic Plants," *Science* 256:520–524 (1992).

Pollard, M.R. et al., "Biosynthesis of C20 and C22 Fatty Acids by Developing Seeds of *Limnanthes alba*," *Plant Physiol.* 66:649–655 (1980).

Post–Beitenmiller, D. et al., "Regulation of Plant Fatty Acid Biosynthesis: Analysis of Acyl–CoA and Acyl–ACP Substrate Pools in Spinach and Pea Chloroplasts," *Plant Physiol.* 100:923–930 (1992).

Post–Beitenmiller, D. et al., "In vivo Pools of Free and Acylated Acyl Carrier Proteins in Spinach. Evidence for Sites of Regulation of Fatty Acid Biosynthesis," *J. Biol. Chem.* 266:1858–1865 (1991).

Rock and Garwin, "Preparative Enzymatic Synthesis and Hydrophobic Chromatography of Acyl–Acyl Carrier Protein," *J. Biol. Chem.* 254:7123–7128 (1979).

Roesler, K.R. et al., "Structure and Expression of an Arabidopsis Acetyl–Coenzyme a Carboxylase Gene," *Plant Physiol.* 105:611–617 (1994).

Roessler, P.G. et al., "Cloning and Characterization of the Gene that Encodes Acetyl–Coenzyme A Carboxylase in the Alga *Cyclotella Cryptica.,*" *J. Biol. Chem.* 268:19254–19259 (1993).

Roughan, G., "Long–Chain Fatty Acid Synthesis and Utilization by Isolated Chloroplasts," *Meth. Enz.* 148:327–337 (1987).

Sambrook, J. et al., *Molecular Cloning: A Laboratory Manual,* Second Edition, vol. 2, Cold Spring Harbor Laboratory Press, Cold Spring, NY, at pp. 8.46–8.47 (1989).

Sasaki, Y. et al., "Chloroplast–Encoded Protein as a Subunit of Acetyl–CoA Carboxylase in Pea Plant," *J. Biol. Chem.* 268:25118–25123 (1993).

Sauer, A. et al., "Regulation of Acetyl–Coenzyme a Carboxylase and Acetyl–Coenzyme a Synthetase in Spinach Chloroplasts," *Z. Naturforsch* 39c:268–275 (1984).

Savage, L.J. et al., "Phosphopantethenylated Precursor Acyl Carrier Protein is Imported into Spinach (*Spinacia oleracea*) Chloroplasts," *Plant Physiol.* 104:989–995 (1994).

Shorrosh, B.S. et al., "The Pea Chloroplast Membrane–Associated Protein, IEP96, is a Subunit of Acetyl–CoA Carboxylase," *Plant. J.* 10:261–268 (1996).

Shorrosh, B.S. et al., "Molecular Cloning of a Putative Plant Endomembrane Protein Resembling Vertebrate Protein Disulfide–Isomerase and a Phosphatidylinositol–Specific Phospholipase C," *PNAS (USA)* 88:10941–10945 (1991).

Shorrosh, B.S. et al., "Structural Analysis, Plastid Localization, and Expression of the Biotin Carboxylase Subunit of Acetyl–Coenzyme A Carboxylase from Tobacco," *Plant Physiol.* 108:805–812 (1995).

Shorrosh, B.S. et al., "Molecular Cloning, Characterization, and Elicitation of Acetyl–CoA Carboxylase from Alfalfa," *PNAS (USA)* 91:4323–4327 (1994).

Song, J. et al., "Molecular Cloning and Characterization of the cDNA Coding for the Biotin–Containing Subunit of 3–Methylcrotonoyl–CoA Carboxylase: Identification of the Biotin Carboxylase and Biotin–Carrier Domains," *PNAS (USA)* 91:5779–5783 (1994).

Takai, T. et al., "Primary Structure of Chicken Liver Acetyl–Coenzyme A Carboxylase deduced from cDNA Sequence," *J. Biol. Chem.* 263:2651–2657 (1988).

van de Loo, F.T. et al., "Express Sequence Tags from Developing Castor Seeds," *Plant Physiol.* 108:1141–1150 (1995).

Wurtele, E.S. et al., "Differential Accumulation of Biotin Enzymes During Carrot Somatic Embryogenesis," *Plant Physiol.* 99:1699–1703 (1992).

Elborough et al. *The Biochemical Journal* 301:599–605, 1994.

```
                                                         ctagctccgccctc              14
tctcttctctgtcaaagtaaatagttcttggcaggaatacaggaattagattacattgatcaggaaa                  84
ATGGACTCGGCAGCCCTGACTAGCGTTTGTGGGCAAATCTGCTCTTCGCTTCACTCCGGGTTTATTCTGG              154
 m  d  s  a  a  l  t  s  v  c  g  k  s  a  l  r  f  t  p  g  l  f  l  q            24
GGAGAACCAATGGTATTAGGAGCTCGCAGTGTAGCTTTATGGCAGGAAACCGGATAAACTTTCCGCGGCA              224
 r  t  n  g  i  r  s  s  q  c  s  f  m  a  g  n  r  i  n  f  p  r  q               47
                                                         SacI NdeI
                                                         gagctccatatgCGC             294
GAGAGCTCAAGCATATAGAGTTAGTACTAAATCTAGCACACGTGGTGCTCTTGCTGCTGTGGTGCAACATGTCGC
 r  a  q  a  y  r  v  s  t  k  s  s  t  r  g  g  a  l  a  A  T  C  R               70
     J0288
     GCCGAGAAGATTCTGGT
GCCGAGAAGATTCTGGTGGTGGCAAATCGAGGAGAGAAATTGCTGTTCGTGTGATTCGAACTGCCCATGAGATGG        364
 A  E  K  I  L  V  A  N  R  G  E  I  A  V  R  V  I  R  T  A  H  E  M  G            94
GAATTCCTTGTGTTGCTGTTTATTCGACCATAGACAAAGATGCCTTACATGTGAAGCTAGCTGATGAATC             434
 I  P  C  V  A  V  Y  S  T  I  D  K  D  A  L  N  V  K  L  A  D  E  S               117
TGTTTGCATTGGTGAAGCACCAAGCAATCAATCGTATTTAGTGATCCCAAATGTCTTATCTGCTGCTATC             504
 V  C  I  G  E  A  P  S  N  Q  S  Y  L  V  I  P  N  V  L  S  A  A  I               140
```

*FIG. 1*

```
AGTCGTGGATGTACAATGTTGCATCCTGGATATGGTTTCCTTGCTGAGAATGCAGTTTTTGTTGAGATGT  574
 S  R  G  C  T  M  L  H  P  G  Y  G  F  L  A  E  N  A  V  P  V  E  M  C   164

GCAGAGAACATGGAATCAACTTTATTGGGCCAAATCCAGACAGTATTAGAGTCATGGGTGACAAATCCAC  644
 R  E  N  G  I  N  F  I  G  P  N  P  D  S  I  R  V  K  G  D  K  S  T     187

TGCCAGAGATACAATGAAGAATGCTGGTGTGTTCCAACTGTGCCAGGAAGTGATGGACTATTACAGAGCACT  714
 A  R  D  T  M  K  N  A  G  V  P  T  V  P  G  S  D  G  L  L  Q  S  T     210

GAAGAAGGTGTAAGGCTTGCTGAGGAGATTGGTTACCCTGTGATGATTAAGGCAACAGCTGGTGGTGGTG  784
 E  E  G  V  R  L  A  E  E  I  G  Y  P  V  M  I  K  A  T  A  G  G  G  C   234

GACGTGGAATGCGTCTTGCTAAAGAACCTGATGAGTTTGTAAAATTATTACAGCAAGCTAAAAGTGAAGC  854
 R  G  M  R  L  A  K  E  P  D  E  F  V  K  L  L  Q  Q  A  K  S  E  A      257
                                                            AvrII

AGCTGCTGCATTTGGAAATGATGCCGTTTATCTGGAGAAGTACGTCCAAAATCCAAGACATTGAATTT  924
 A  A  A  F  G  N  D  G  V  Y  L  E  K  Y  V  Q  N  P  R  H  I  K  F      280

CAGGTTTTGGCGGACAAGTATGGTAATGTTGTACACTTTGGAGAGCGTGATTGCAGTATTCAGAGAAGGA  994
 Q  V  L  A  D  K  Y  G  N  V  V  H  F  G  E  R  D  C  S  I  Q  R  R  N   304

ACCAGAAGTTGCTCGAGGAAGCACCTTCCCCTGCATTAACACCAGAGCTAAGGAACGCCATGGGTGACGC 1064
 Q  K  L  E  E  A  P  S  P  A  L  T  P  E  L  R  N  A  K  G  D  A        327
```

FIG. 1
(CONTINUED)

```
AGCTGTTGCGGCAGCAGCATCCATAGGTTACATTGGTGTTGGTACCGTGGAGTTCCTATTGGATGAGAGA  1134
 A  V  A  A  A  A  S  I  G  Y  I  G  V  V  G  T  V  E  F  L  L  D  E  R   350

GGGTCCTTTTACTTCATGGAAATGAACACTCGTATTCAGGTAGAGCATCCAGTGACAGAAATGATATCCT  1204
 G  S  F  Y  F  M  E  K  N  T  R  I  Q  V  E  M  P  V  T  E  K  I  S     374

CTGTTGATCTGATAGAGGAACAGATCCGTGTGGCTATGGGAGAAAAGCTCCGATACAAACAGGAGGATAT  1274
 V  D  L  I  E  K  Q  I  R  V  A  M  G  E  K  L  R  Y  K  Q  E  D  I     397

TGTGCTTAGAGGACATTCAATTGAATGCCGTATAAATGCAGAAGATGCTTTCAAAAATTTCAGACCCGGA  1344
 V  L  R  G  H  S  I  E  C  R  I  N  A  E  D  A  F  K  N  F  R  P  G     420

CCAGGGAGAATCACTGCCTATTTACCAGCTGGAGGTCCATTGTGCGTATGGATAACCACGTTTATCCTG  1414
 P  G  R  I  T  A  Y  L  P  A  G  G  P  F  V  R  K  D  N  K  V  Y  P  D   444

ACTATGTGGTTCCACCTAGCGACGATTCCCTGCTAGGAAAGCTCATCGTATGGGCTCCAACACGCGAGGG  1484
 Y  V  V  P  P  S  D  D  S  L  L  G  K  L  I  V  W  A  P  T  R  E  G     467

GGCTATTGAACGCATGAAAAGAGCACTTAATGACACCATAATTACTGGAGTTCCTACCACAATAGAATAT  1554
 A  I  E  R  M  K  R  A  L  N  D  T  I  I  T  G  V  P  T  T  I  E  Y     490

CATAAGCTCATCCTCGATATTGAGGACTTTAAGAATGGAAAGTTTGATCCTTCTTTTATTCCCAAGCATG  1624
 N  K  L  I  L  D  I  E  D  F  K  N  G  K  F  D  P  S  F  I  P  K  N  G   514

GAGGAGAATTAGCTCCCCCCCACAAAATGGTTCCAGCAGCTACCAAGGAGATGGTCAATGCTAGTGCTTA  1694
 G  E  L  A  P  P  N  K  M  V  P  A  A  T  K  E  N  V  N  A  S  A  V     536
```

FIG. 1 *(CONTINUED)*

```
attcttcctctcttttttttttttttttcttgatattttcttacccttgtcggcgaatagtgaaa  1764
gcagattgctcccattggatcttgaggtgactgcagttctggatataacattcatctcttgatcttagc  1834
                      ctccactgacatcaagacctaAGATCTTA
                           J0280      XbaI
ttgaatgtattttagatacacactagactgaatgaaattctttttggtatatgatgctcaatcgaatct  1904
gtgttaaatggcaaagaaaaaaaaaaaaaaaaaaaaa  1957
```

FIG. 1
*(CONTINUED)*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1921 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (A) ORGANISM: biotin carboxylase subunit
      (B) STRAIN: nicotiana tabacum (vii) IMMEDIATE SOURCE:
      (B) CLONE: E3

(ix) FEATURE:
      (A) NAME/KEY: CDS
      (B) LOCATION: 85..1695

(x) PUBLICATION INFORMATION:
      (A) AUTHORS: Shorrosh, Basil S.
         Roesler, Keith R.
         Shintani, D.
         van de Loo, F. J.
         Ohlrogge, John B.
      (B) TITLE: Structural analysis, plastid localization,
         and expression of the biotin carboxylase subunit
         of acetyl-coenzyme A carboxylase from tobacco
      (C) JOURNAL: Plant Physiol.
      (D) VOLUME: 108
      (E) ISSUE: 2
      (F) PAGES: 805-812
      (G) DATE: 1995
      (K) RELEVANT RESIDUES IN SEQ ID NO:1: FROM 1 TO 1921

(xi) SEQUENCE DESCRIPTION: SEQ ID NO:1:

```
CTAGCTCCGC CCTCTCTCTT TCTCTCTGTC AAAGTAAATA GTTCTTGGCA GGAATACAGG        60

AATTAGATTA CATTGATCAG GAAA ATG GAC TCG GCA GCC CTG ACT AGC GTT         111
                           Met Asp Ser Ala Ala Leu Thr Ser Val
                             1               5

TGT GGC AAA TCT GCT CTT CGC TTC ACT CCG GGT TTA TTT CTG GGG AGA        159
Cys Gly Lys Ser Ala Leu Arg Phe Thr Pro Gly Leu Phe Leu Gly Arg
 10              15                  20                  25

ACG AAT GGT ATT AGG AGC TCG CAG TGT AGC TTT ATG GCA GGA AAC CGG        207
Thr Asn Gly Ile Arg Ser Ser Gln Cys Ser Phe Met Ala Gly Asn Arg
             30                  35                  40
```

```
ATA AAC TTT CCG CGG CAG AGA GCT CAA GCA TAT AGA GTT AGT ACT AAA      255
Ile Asn Phe Pro Arg Gln Arg Ala Gln Ala Tyr Arg Val Ser Thr Lys
            45                  50                  55

TCT AGC ACA CGT GGT GGT GCT CTT GCT GCA ACA TGT CGC GCC GAG AAG      303
Ser Ser Thr Arg Gly Gly Ala Leu Ala Ala Thr Cys Arg Ala Glu Lys
            60                  65                  70

ATT CTG GTG GCA AAT CGA GGA GAA ATT GCT GTT CGT GTG ATT CGA ACT      351
Ile Leu Val Ala Asn Arg Gly Glu Ile Ala Val Arg Val Ile Arg Thr
        75                  80                  85

GCC CAT GAG ATG GGA ATT CCT TGT GTT GCT GTT TAT TCG ACC ATA GAC      399
Ala His Glu Met Gly Ile Pro Cys Val Ala Val Tyr Ser Thr Ile Asp
90              95                  100                 105

AAA GAT GCC TTA CAT GTG AAG CTA GCT GAT GAA TCT GTT TGC ATT GGT      447
Lys Asp Ala Leu His Val Lys Leu Ala Asp Glu Ser Val Cys Ile Gly
                110                 115                 120

GAA GCA CCA AGC AAT CAA TCG TAT TTA GTG ATC CCA AAT GTC TTA TCT      495
Glu Ala Pro Ser Asn Gln Ser Tyr Leu Val Ile Pro Asn Val Leu Ser
                125                 130                 135

GCT GCT ATC AGT CGT GGA TGT ACA ATG TTG CAT CCT GGA TAT GGT TTC      543
Ala Ala Ile Ser Arg Gly Cys Thr Met Leu His Pro Gly Tyr Gly Phe
            140                 145                 150

CTT GCT GAG AAT GCA GTT TTT GTT GAG ATG TGC AGA GAA CAT GGA ATC      591
Leu Ala Glu Asn Ala Val Phe Val Glu Met Cys Arg Glu His Gly Ile
155                 160                 165

AAC TTT ATT GGG CCA AAT CCA GAC AGT ATT AGA GTC ATG GGT GAC AAA      639
Asn Phe Ile Gly Pro Asn Pro Asp Ser Ile Arg Val Met Gly Asp Lys
170                 175                 180                 185

TCC ACT GCC AGA GAT ACA ATG AAG AAT GCT GGT GTT CCA ACT GTG CCA      687
Ser Thr Ala Arg Asp Thr Met Lys Asn Ala Gly Val Pro Thr Val Pro
                190                 195                 200

GGA AGT GAT GGA CTA TTA CAG AGC ACT GAA GAA GGT GTA AGG CTT GCT      735
Gly Ser Asp Gly Leu Leu Gln Ser Thr Glu Glu Gly Val Arg Leu Ala
                205                 210                 215

GAG GAG ATT GGT TAC CCT GTG ATG ATT AAG GCA ACA GCT GGT GGT GGT      783
Glu Glu Ile Gly Tyr Pro Val Met Ile Lys Ala Thr Ala Gly Gly Gly
            220                 225                 230

GGA CGT GGA ATG CGT CTT GCT AAA GAA CCT GAT GAG TTT GTA AAA TTA      831
Gly Arg Gly Met Arg Leu Ala Lys Glu Pro Asp Glu Phe Val Lys Leu
235                 240                 245

TTA CAG CAA GCT AAA AGT GAA GCA GCT GCT GCA TTT GGA AAT GAT GGC      879
Leu Gln Gln Ala Lys Ser Glu Ala Ala Ala Ala Phe Gly Asn Asp Gly
250                 255                 260                 265

GTT TAT CTG GAG AAG TAC GTC CAA AAT CCT AGG CAC ATT GAA TTT CAG      927
Val Tyr Leu Glu Lys Tyr Val Gln Asn Pro Arg His Ile Glu Phe Gln
                270                 275                 280

GTT TTG GCG GAC AAG TAT GGT AAT GTT GTA CAC TTT GGA GAG CGT GAT      975
Val Leu Ala Asp Lys Tyr Gly Asn Val Val His Phe Gly Glu Arg Asp
            285                 290                 295

TGC AGT ATT CAG AGA AGG AAC CAG AAG TTG CTG GAG GAA GCA CCT TCC     1023
Cys Ser Ile Gln Arg Arg Asn Gln Lys Leu Leu Glu Glu Ala Pro Ser
            300                 305                 310

CCT GCA TTA ACA CCA GAG CTA AGG AAC GCC ATG GGT GAC GCA GCT GTT     1071
Pro Ala Leu Thr Pro Glu Leu Arg Asn Ala Met Gly Asp Ala Ala Val
            315                 320                 325

GCG GCA GCA GCA TCC ATA GGT TAC ATT GGT GTT GGT ACC GTG GAG TTC     1119
Ala Ala Ala Ala Ser Ile Gly Tyr Ile Gly Val Gly Thr Val Glu Phe
330                 335                 340                 345

CTA TTG GAT GAG AGA GGG TCC TTT TAC TTC ATG GAA ATG AAC ACT CGT     1167
Leu Leu Asp Glu Arg Gly Ser Phe Tyr Phe Met Glu Met Asn Thr Arg
```

-continued

```
                  350                 355                 360
ATT CAG GTA GAG CAT CCA GTG ACA GAA ATG ATA TCC TCT GTT GAT CTG         1215
Ile Gln Val Glu His Pro Val Thr Glu Met Ile Ser Ser Val Asp Leu
            365                 370                 375

ATA GAG GAA CAG ATC CGT GTG GCT ATG GGA GAA AAG CTC CGA TAC AAA         1263
Ile Glu Glu Gln Ile Arg Val Ala Met Gly Glu Lys Leu Arg Tyr Lys
            380                 385                 390

CAG GAG GAT ATT GTG CTT AGA GGA CAT TCA ATT GAA TGC CGT ATA AAT         1311
Gln Glu Asp Ile Val Leu Arg Gly His Ser Ile Glu Cys Arg Ile Asn
        395                 400                 405

GCA GAA GAT GCT TTC AAA AAT TTC AGA CCC GGA CCA GGG AGA ATC ACT         1359
Ala Glu Asp Ala Phe Lys Asn Phe Arg Pro Gly Pro Gly Arg Ile Thr
410                 415                 420                 425

GCC TAT TTA CCA GCT GGA GGT CCA TTT GTG CGT ATG GAT AAC CAC GTT         1407
Ala Tyr Leu Pro Ala Gly Gly Pro Phe Val Arg Met Asp Asn His Val
                430                 435                 440

TAT CCT GAC TAT GTG GTT CCA CCT AGC GAC GAT TCC CTG CTA GGA AAG         1455
Tyr Pro Asp Tyr Val Val Pro Pro Ser Asp Asp Ser Leu Leu Gly Lys
                445                 450                 455

CTC ATC GTA TGG GCT CCA ACA CGC GAG GGG GCT ATT GAA CGC ATG AAA         1503
Leu Ile Val Trp Ala Pro Thr Arg Glu Gly Ala Ile Glu Arg Met Lys
            460                 465                 470

AGA GCA CTT AAT GAC ACC ATA ATT ACT GGA GTT CCT ACC ACA ATA GAA         1551
Arg Ala Leu Asn Asp Thr Ile Ile Thr Gly Val Pro Thr Thr Ile Glu
        475                 480                 485

TAT CAT AAG CTC ATC CTC GAT ATT GAG GAC TTT AAG AAT GGA AAG TTT         1599
Tyr His Lys Leu Ile Leu Asp Ile Glu Asp Phe Lys Asn Gly Lys Phe
490                 495                 500                 505

GAT CCT TCT TTT ATT CCC AAG CAT GGA GGA GAA TTA GCT CCC CCC CAC         1647
Asp Pro Ser Phe Ile Pro Lys His Gly Gly Glu Leu Ala Pro Pro His
                510                 515                 520

AAA ATG GTT CCA GCA GCT ACC AAG GAG ATG GTC AAT GCT AGT GCT             1692
Lys Met Val Pro Ala Ala Thr Lys Glu Met Val Asn Ala Ser Ala
                525                 530                 535

TAATTCTTCC TCTTTTTTTT TTTTTTTTTT TCTTTGATAT TTTTCCTTTA CCCTTGTCGG       1752

CGAATAGTGA AAGCAGATTG CTCCCATTGG ATCTTGAGGT GACTGCAGTT CTGGATATAA       1812

CATTCATCTC TTTGATCTTA GCTTGAATGT ATTTTTAGAT ACACTAGACT GAATGAAATT       1872

CTTTTTTTGG TATATGATGC TCAATCGAAT CTGTGTTAAA TGGCAAAAG                   1921
```

(2) INFORMATION FOR SEQ ID NO:2:

(i) SEQUENCE CHARACTERISTICS:
        (A) LENGTH: 536 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Ser Ala Ala Leu Thr Ser Val Cys Gly Lys Ser Ala Leu Arg
 1               5                  10                  15

Phe Thr Pro Gly Leu Phe Leu Gly Arg Thr Asn Gly Ile Arg Ser Ser
            20                  25                  30

Gln Cys Ser Phe Met Ala Gly Asn Arg Ile Asn Phe Pro Arg Gln Arg
        35                  40                  45

Ala Gln Ala Tyr Arg Val Ser Thr Lys Ser Ser Thr Arg Gly Gly Ala
    50                  55                  60

Leu Ala Ala Thr Cys Arg Ala Glu Lys Ile Leu Val Ala Asn Arg Gly
```

-continued

```
                65                  70                  75                  80
            Glu Ile Ala Val Arg Val Ile Arg Thr Ala His Glu Met Gly Ile Pro
                            85                  90                  95
            Cys Val Ala Val Tyr Ser Thr Ile Asp Lys Asp Ala Leu His Val Lys
                        100                 105                 110
            Leu Ala Asp Glu Ser Val Cys Ile Gly Glu Ala Pro Ser Asn Gln Ser
                        115                 120                 125
            Tyr Leu Val Ile Pro Asn Val Leu Ser Ala Ala Ile Ser Arg Gly Cys
                        130                 135                 140
            Thr Met Leu His Pro Gly Tyr Gly Phe Leu Ala Glu Asn Ala Val Phe
            145                 150                 155                 160
            Val Glu Met Cys Arg Glu His Gly Ile Asn Phe Ile Gly Pro Asn Pro
                        165                 170                 175
            Asp Ser Ile Arg Val Met Gly Asp Lys Ser Thr Ala Arg Asp Thr Met
                        180                 185                 190
            Lys Asn Ala Gly Val Pro Thr Val Pro Gly Ser Asp Gly Leu Leu Gln
                        195                 200                 205
            Ser Thr Glu Glu Gly Val Arg Leu Ala Glu Glu Ile Gly Tyr Pro Val
                        210                 215                 220
            Met Ile Lys Ala Thr Ala Gly Gly Gly Arg Gly Met Arg Leu Ala
            225                 230                 235                 240
            Lys Glu Pro Asp Glu Phe Val Lys Leu Leu Gln Gln Ala Lys Ser Glu
                        245                 250                 255
            Ala Ala Ala Ala Phe Gly Asn Asp Gly Val Tyr Leu Glu Lys Tyr Val
                        260                 265                 270
            Gln Asn Pro Arg His Ile Glu Phe Gln Val Leu Ala Asp Lys Tyr Gly
                        275                 280                 285
            Asn Val Val His Phe Gly Glu Arg Asp Cys Ser Ile Gln Arg Arg Asn
                        290                 295                 300
            Gln Lys Leu Leu Glu Glu Ala Pro Ser Pro Ala Leu Thr Pro Glu Leu
            305                 310                 315                 320
            Arg Asn Ala Met Gly Asp Ala Ala Val Ala Ala Ala Ser Ile Gly
                        325                 330                 335
            Tyr Ile Gly Val Gly Thr Val Glu Phe Leu Leu Asp Glu Arg Gly Ser
                        340                 345                 350
            Phe Tyr Phe Met Glu Met Asn Thr Arg Ile Gln Val Glu His Pro Val
                        355                 360                 365
            Thr Glu Met Ile Ser Ser Val Asp Leu Ile Glu Glu Gln Ile Arg Val
                        370                 375                 380
            Ala Met Gly Glu Lys Leu Arg Tyr Lys Gln Glu Asp Ile Val Leu Arg
            385                 390                 395                 400
            Gly His Ser Ile Glu Cys Arg Ile Asn Ala Glu Asp Ala Phe Lys Asn
                        405                 410                 415
            Phe Arg Pro Gly Pro Gly Arg Ile Thr Ala Tyr Leu Pro Ala Gly Gly
                        420                 425                 430
            Pro Phe Val Arg Met Asp Asn His Val Tyr Pro Asp Tyr Val Val Pro
                        435                 440                 445
            Pro Ser Asp Asp Ser Leu Leu Gly Lys Leu Ile Val Trp Ala Pro Thr
                        450                 455                 460
            Arg Glu Gly Ala Ile Glu Arg Met Lys Arg Ala Leu Asn Asp Thr Ile
            465                 470                 475                 480
            Ile Thr Gly Val Pro Thr Thr Ile Glu Tyr His Lys Leu Ile Leu Asp
                        485                 490                 495
```

```
-continued

Ile Glu Asp Phe Lys Asn Gly Lys Phe Asp Pro Ser Phe Ile Pro Lys
            500                 505                 510

His Gly Gly Glu Leu Ala Pro Pro His Lys Met Val Pro Ala Ala Thr
        515                 520                 525

Lys Glu Met Val Asn Ala Ser Ala
    530                 535
```

STRUCTURE AND EXPRESSION OF THE BIOTIN CARBOXYLASE SUBUNIT OF HETEROMERIC ACETYL-COA CARBOXYLASE

SPONSORSHIP

Work on this invention was sponsored in part by National Science Foundation Grants DCB 90-05290 and 94-06466. The Government may have certain rights in the invention.

FIELD OF THE INVENTION

The present invention relates generally to the biotin carboxylase subunit of acetyl-CoA carboxylase and more particularly, the biotin carboxylase subunit of heteromeric acetyl-CoA carboxylase from tobacco and its use in controlling the carboxylation of acetyl-CoA.

GENBANK ACCESSION INFORMATION

| GENE | ACCESSION NO. |
| --- | --- |
| Tobacco Biotin Carboxylase Subunit of ACCase | L38260 |

BACKGROUND OF THE INVENTION

Acetyl-coenzyme A (acetyl-CoA) carboxylase (ACCase) is a biotinylated enzyme that catalyzes the ATP-dependent formation of malonyl-CoA from acetyl-CoA and bicarbonate. Malonyl-CoA is an essential substrate for fatty acid biosynthesis in plastids (Harwood, J. L., *Annu. Rev. Plant Physiol. Plant Mol. Biol.* 39:101–138 (1988)) and chain elongation in the cytosol (Pollard, M. et al., *Plant Physiol.* 66:649–655 (1980)). In addition, malonyl-CoA is required in the cytosol for several reactions including the biosynthesis of flavonoids (Ebel, J. et al., *Eur. J. Biochem.* 75:201–209 (1977) and Ebel, J. et al., *Arch. Biochem. Biophys.* 232:240–248 (1984)). It has been shown that the regulation of activity of the plastid ACCase is a major determinant of the flux of carbon into fatty acid synthesis in spinach (Post-Beittenmiller, D. et al., *J. Biol. Chem.* 266:1858–1865 (1991) and Post-Beittenmiller, D. et al., *Plant Physiol.* 100:923–930 (1992)) and in barley or maize leaves (Page, R.A. et al., *Biochem. Biophys.* 1210:369–372 (1994)). Two forms of ACCase, termed "prokaryotic" and "eukaryotic," have been isolated and characterized. The prokaryotic form is a heteromeric chloroplast enzyme (also referred to as a multi-subunit (MS) enzyme) composed of dissociable subunits. For example, *E. coli* ACCase is composed of four subunits: the biotin carboxylase (BC), the biotin carboxyl carrier protein (BCCP), and the carboxyltransferase (CT) α- and β-subunits (Li, S-J. et al., *J. Bio. Chem.* 267:855–863 (1992); Li, S-J. et al., *J. Bio. Chem.* 267:16841–16847 (1992); Kondo, H. et al., *PNAS (USA)* 88:9730–9733 (1989) and Alix, J-H. et al., *DNA* 8:779–789 (1989)). The eukaryotic form of ACCase is a homomeric, presumably cytosolic enzyme (also referred to as multi-functional (MF) enzyme) containing the BC, BCCP, and CT functional domains with a molecular weight of more than 200 kDa. The full-length homomeric ACCase has been cloned from mammals (Takai, T. et al., *J. Biol Chem.* 263:2651–2657 (1988); Lopez-Casillas, F. et al., *PNAS (USA)* 85:5784–5788 (1988); Ha, J. et al., *Eur. J. Biochem.* 219:297–306 (1994)), yeast (Al-Feel, W. et al., *PNAS (USA)* 89:4534–4538 (1992)), algae (Roessler, P. G. et al., *J. Biol. Chem.* 268:19254–19259 (1993)) and plants (Shorrosh, B. S. etal., *PNAS (USA)* 91:4323–4327 (1994); Roesler, K. R. et al., *Plant Physiol.* 105:611–617 (1994) and Gornicki, P. et al., *PNAS (USA)* 91:6860–6864 (1994)). Partial homomeric ACCase sequences have also been reported from several plants (Elborough, K. M. et al., *Plant Mol. Biol.* 24:21–34 (1994) and Ashton, A. R. et al., *Plant Mol. Biol.* 24:35–49 (1994)). To date, all homomeric ACCase sequences reported from plants show high sequence identity in their encoded amino acid sequences. Thus, there is currently no sequence evidence for differences, if any, between plastidial and cytosolic forms of homomeric ACCase. Preliminary evidence suggested that the alfalfa and Arabidopsis homomeric ACCases are localized in the cytosol (Shorrosh, B. S. et al., *PNAS (USA)* 91:4323–4327 (1994) and Roesler, K. R. et al., *Plant Physiol.* 105:611–617 (1994)). However, two isoforms of the homomeric ACCase have been characterized from maize based on their chloroplastic and extra-chloroplastic localization and their herbicide sensitivity (Egli, M. A. et al., *Plant Physiol.* 101:499–506 (1993)).

Recently it has been shown that homomeric ACCase isolated from young pea leaves is localized in the epidermal tissues (Alban, C. et al., *Biochem. J.* 300:557–565 (1994)). In addition, Western blot analysis using biotin antibodies detected homomeric ACCase in the total protein extract from both Gramineae and dicot plants, but the homomeric ACCase was only present in the chloroplast of Gramineae plants thus reported (Konishi, T. et al., *PNAS (USA)* 91:3598–3601 (1994); Gornicki, P. et al., *J. Bacteriology* 175:5268–5272 (1993); Egli, M. A. et al., *Plant Physiol.* 101:499–506 (1993); Wurtele, E. S. et al., *Plant Physiol.* 99:1699–1703 (1992) and Baldet, P. et al., *Arch. Biochem. Biophys.* 303:67–73 (1993)). Recently, immunological data describing the expression of a pea chloroplast encoded protein, which shares sequence similarity with the *E. coli* carboxyltransferase β-subunit (accD) of ACCase was reported (Sasaki, Y. et al., *J. Biol. Chem.* 268:25118–25123 (1993)). Antibodies against the pea accD-like protein precipitated the activity of pea chloroplast ACCase with the concomitant precipitation of three polypeptides including a 35-kDa biotin-containing protein (Sasaki, Y. et al., *J. Biol. Chem.* 268:25118–25123 (1993)). Also, a heteromeric ACCase enzyme consisting of dissociable subunits with molecular weights ranging from 32 to 79 kDa has been partially purified and characterized from the epidermal and mesophyll tissues of pea leaves. One of these subunits, with a molecular weight of 38 kDa, was biotinylated (Alban, C. et al., *Biochem. J.* 300:557–565 (1994)). Western blot analysis of pea chloroplasts localized only one biotin-containing protein with an apparent molecular weight of 35 to 38 kDa (Sasaki, Y. et al., *J. Biol. Chem.* 268:25118–25123 (1993) and Baldet, P. et al., *Arch. Biochem. Biophys.* 303:67–73 (1993)); others have reported multiple biotin-containing proteins in dicot chloroplasts (Gornicki, P. et al., *J. Bacteriology* 175:5268–5272 (1993) and Wurtele, E. S. et al., *Plant Physiol.* 99:1699–1703 (1992)). Taken together, the reported data suggest that dicot plastids contain heteromeric ACCase; the number of subunits and their organization, however, is not yet understood.

It would thus be desirable to provide the biotin carboxylase subunit of acetyl-CoA carboxylase. It would also be desirable to control expression of the gene encoding the biotin carboxylase subunit of acetyl-CoA carboxylase. It would further be desirable to control the carboxylation of acetyl-CoA to produce malonyl-CoA. It would also be desirable to control the carboxylation of acetyl-CoA to produce malonyl-CoA by controlling the expression of genes encoding the ACCase subunits. It would further be desirable to acquire long-term control of the carboxylation of acetyl-CoA to produce malonyl-CoA by genetically altering plants. It would also be desirable to control fatty acid synthesis in plants and seeds by controlling the carboxylation of acetyl-CoA to produce malonyl-CoA. It would further be desirable to control fatty acid synthesis in plants and seeds without employing foreign chemicals.

SUMMARY OF THE INVENTION

The present invention provides a novel purified and isolated nucleic acid sequence encoding a biotin carboxylase subunit of heteromeric ACCase. Genomic organization, expression, chloroplastic localization and function of the nucleic acid and protein product are also provided. The nucleic acid sequence is set forth in FIG. 1 and has been accorded GenBank Accession No. L38260. The deduced amino acid sequence is also set forth in FIG. 1. Vectors comprising the nucleic acid sequence of the present invention, plant cells transformed with the vectors, as well as plants containing the vectors and seeds of the transgenic plants are also provided.

The nucleotide sequences of the present invention may be used to control carboxylation of acetyl-CoA to produce malonyl-CoA. Thus, by introducing constructs of the gene of the present invention in sense or anti-sense orientation, carboxylation of acetyl-CoA to produce malonyl-CoA may be increased or decreased. Consequently, fatty acid synthesis and elongation in plants and seeds which is dependent on malonyl-CoA may also be increased or decreased. Secondary metabolite production in plants which is also dependent on acetyl-CoA and malonyl-CoA may also be controlled. Moreover, long-term control of the carboxylation of acetyl-CoA to produce malonyl-CoA may be obtained by genetically altering plants with the nucleotide sequences of the present invention.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIG. 1 is the nucleotide sequence and the deduced amino acid sequence of the plant biotin carboxylase subunit of heteromeric ACCase of the present invention;

DETAILED DESCRIPTION OF THE PREFERRED EMBODIMENTS

Figure 2:
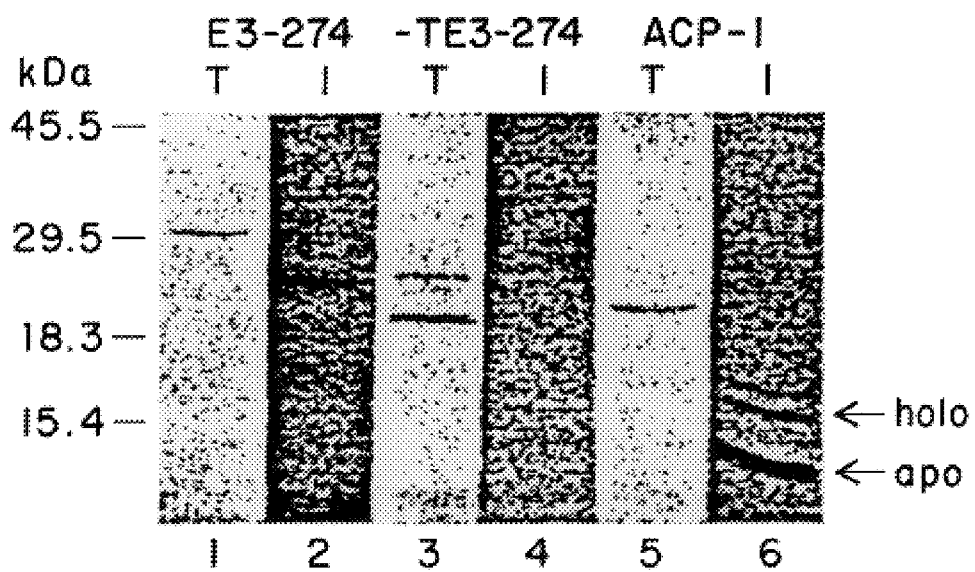
FIG. 2 is a photograph of a gel showing the results of a chloroplast uptake experiment.

A novel purified and isolated nucleic acid sequence encoding a biotin carboxylase subunit of heteromeric ACCase is provided. It has been shown that the nucleic acid sequence of the present invention encodes a 50-kDa biotin carboxylase subunit of heteromeric ACCase located in the plastid of tobacco plants (Nicotiana tabacum L. cv bright yellow 2). Sequences of the present invention may therefore be used to increase and decrease the carboxylation of acetyl-CoA to produce malonyl-CoA in the plastid of plants, thereby increasing and decreasing fatty acid synthesis. A method of controlling carboxylation of acetyl-CoA to produce malonyl-CoA and controlling fatty acid synthesis is thus provided by the present invention. Vectors containing the nucleic acid sequence of the present invention, plant cells transformed with the vectors of the present invention as well as plants containing the sequences of the present invention and seeds produced thereby, are also within the scope of the present invention.

The methods of the present invention generally comprise the step of introducing in sense or antisense orientation the gene described herein into a plant cell and growing the cell into a plant. It will be appreciated that other genes (both sense and antisense orientation) may also be introduced into the plant cell, e.g., genes encoding the other subunits of the heteromeric form of ACCase. A gene in sense or antisense orientation may be fused to a gene or fragment thereof which allows the gene to be transported and expressed in a plant cell. The gene or gene fragment in sense or anti-sense orientation is referred to as a "construct" herein. It will be appreciated that the constructs of the present invention may contain any regulatory elements necessary and known to those skilled in the art for expression of the gene in either orientation. For example, constructs prepared with either seed-specific promoters such as the napin seed storage protein promoter of rapeseed, or with a constitutive promoter such as the cauliflower mosaic virus 35 S (CaMV35S) promoter, are contemplated by the present invention.

It is believed that seed-specific promoters may be more desirable and effective in altering seed oil amounts or composition by avoiding possible deleterious effects in the plant. The constitutive promoter, however, may be more effective in, for example, engineering general herbicide resistance in the whole plant. Plants of the Gramineae family are extremely sensitive to certain "grass-selective" herbicides. This sensitivity is known to result from the inhibition of the homomeric ACCase. Certain grass biotypes which are partially resistant to the herbicides have been shown to have altered ACCase. The heteromeric ACCase is completely resistant to the "grass-selective" herbicides. Therefore, introduction of the gene of the present invention into Gramineae plants such as Gramineae grasses (e.g., corn, wheat, barley, oats, etc.), can provide resistance in these species to such herbicides. It will be appreciated that genes encoding the other subunits of the heteromeric ACCase may also be introduced in addition to or in combination with the gene of the present invention. Because herbicides are usually applied as foliar or ground applications it is necessary for the vegetative parts of the plant to be resistant. Therefore, a constitutive promoter, such as CaMV35S would be used to create such transgenic plants.

Because malonyl-CoA is required for fatty acid synthesis and elongation in plants and seeds, the present invention also provides a method of controlling plant and seed fatty acid synthesis and elongation. Increasing seed fatty acid synthesis by overexpressing the gene is useful in increasing oil content of rapeseed, soybean, or other oilseed crops. In Brassica seeds, overexpression of the homomeric ACCase increases the malonyl-CoA/acetyl-CoA ratio and increases the amount of oil stored in the seeds. Because the homomeric ACCase is a 250 kDa protein, achieving high levels of expression and successfully targeting to the plastid at sufficiently high expression levels, may be more difficult than the overexpression of heteromeric ACCase. Increasing oil content of oil seeds by overexpressing the gene of the present invention is therefore advantageous. In addition, because the heteromeric ACCase gene described herein encodes a plastid protein and, since fatty acid synthesis takes place primarily in the plastid, a construct which includes the gene described herein does not require a plant plastid transit peptide. An effective increase in ACCase activity in the plastid thus results when the plastid ACCase gene of the present invention is overexpressed. It should be appreciated that decreasing seed fatty acid synthesis by decreasing gene expression is also useful in producing "low-fat" seeds such as low-fat peanuts.

As previously discussed, acetyl-CoA and malonyl-CoA are precursors of various plant secondary metabolites. Thus, increasing expression of the ACCase gene of the present invention increases the amount of malonyl-CoA available for synthesis of flavonoids, isoflavonoids, and other secondary metabolites. Conversely, decreasing expression of the ACCase gene of the present invention may decrease the amount of malonyl-CoA present and increase the amount of acetyl-CoA present. Thus, altering expression of the ACCase gene of the present invention could favorably alter the amount of acetyl-CoA or malonyl-CoA available for production of secondary plant products, many of which have value in plant protection against pathogens, or for medicinal or other uses. Furthermore, it is not necessary that these products be naturally present in plants. For example, bacterial genes may be introduced into plants to produce polyhydroxybutyrate which can be used to synthesize biodegradable plastics. Poirier Y. et al., *Science* 256:520–524 (1992). Production of polyhydroxybutyrate or other acetyl-CoA derived products in a plant will require adequate supply of cellular and plastidial acetyl-CoA. If the fatty acid synthesis pathway is drawing on this acetyl-CoA supply for oil storage, the amount available for alternative, higher-value products will be less. Therefore, inhibition of the fatty acid synthesis pathway may be desirable to allow diversion of more carbon into products other than fatty acids, e.g., increasing the acetyl-CoA to malonyl-CoA ratio by decreasing ACCase gene expression may allow more carbon flux into polyhydroxybutyrate production thereby resulting in higher yields of polyhydroxybutyrate or other acetyl-CoA derived products.

It will be appreciated that the methods of the present invention further include introducing the constructs of the present invention including the sense or antisense orientation of the gene of the present invention, into a plant cell, and growing the cell into a callus and then into a plant; or, alternatively, breeding a transgenic plant produced from the above method with a second plant to form an F1 or higher hybrid (e.g., F2). For example, constructs containing the nucleotide sequences of the present invention may be introduced into plants by cocultivation with Agrobacterium containing the construct. Transgenic plants are therefore produced by the methods of the present invention and are also contemplated by the present invention.

As referred to herein, the term "gene" is meant a nucleic acid, either genomic or synthetic, which encodes a protein product. The term "nucleic acid" is intended to mean natural and synthetic linear and sequential arrays of nucleotides and nucleosides, e.g., in cDNA, genomic DNA (gDNA), mRNA, and RNA, oligonucleotides, oligonucleosides, and derivatives thereof. Thus, alternate nucleic acid forms such as genomic DNA, cDNA and DNA prepared by partial or total chemical synthesis from nucleotides, as well as DNA with mutations, are also within the contemplation of the invention.

The term "sense orientation" as used herein refers to the orientation of a gene such that its RNA transcript, following removal of introns, is translatable into the polypeptide product of the gene. The term "antisense orientation" is used to mean the opposite orientation of a gene such that its transcript is complementary to the normal transcript of the gene when in sense orientation. In addition, the term "encoding" is intended to mean that the subject nucleic acid may be transcribed and translated into either the desired polypeptide or the subject protein in an appropriate expression system, e.g., when the subject nucleic acid is linked to appropriate control sequences such as promoters, operators, regulators, and the like, in a suitable vector (e.g., an expression vector) and when the vector is introduced into an appropriate system or cell.

By "substantially represented by" or "substantially complementary to" as used herein is meant any variation therein which does not impair the functionability of the sequence to any significant degree. By "substantially as shown" or "substantially similar" with respect to a nucleic acid is meant sufficiently similar in structure or sequence to encode the desired polypeptide or gene product, or with respect to a polypeptide, sufficiently similar in structure or sequence to serve its principal function. It will thus be appreciated that the term "polypeptides" includes not only full length protein molecules but also fragments thereof which, by themselves or with other fragments, generate substantially similar physiological activity as the full length protein. It will further be appreciated that synthetic polypeptides of the novel protein of the present invention are also within the scope of the invention and can be manufactured according to standard synthetic methods.

The terms "oilseed plant" and "oilseed crop" are used interchangeably herein and refer to those plants and crops known to those skilled in the art as part of the oilseed variety, including but not limited to rapeseed, soybean, Crambe, mustard, castor bean, peanut, sesame, cottonseed, linseed and sunflower.

The term "capable of hybridizing under stringent conditions" is used to mean annealing a first nucleic acid to a second nucleic acid under stringent conditions (defined below). For example, the first nucleic acid may be a test sample, and the second nucleic acid may be a portion of the nucleic acid sequence set forth in FIG. 1. Hybridization of the first and second nucleic acids is conducted under stringent conditions, e.g., high temperature and/or low salt content, which tend to disfavor hybridization of dissimilar nucleotide sequences. A suitable protocol involves hybridization in 5× SSC at 65° C. in aqueous solution, or 42° C. in formamide, followed by washing with 0.1× SSC at 65° C. in aqueous solution. (Other experimental conditions for controlling stringency are described in Maniatis, T., et al., *Molecular Cloning: A Laboratory Handbook*, Cold Spring Harbor Laboratory Press, Cold Spring, N.Y., (1982), at pages 387–389; and also in Sambrook, J. et al., *Molecular Cloning: A Laboratory Manual, Second Edition*, Volume 2, Cold Spring Harbor Laboratory Press, Cold Spring, N.Y., at pages 8.46–8.47 (1989)). It will be appreciated, however, that although reference herein is made to nucleic acids capable of hybridizing under stringent conditions, hybridization in the practice of the present invention need not actually be conducted under such conditions.

The following Specific Examples and Discussion further explains the present invention.

SPECIFIC EXAMPLE 1

Materials and Methods

Screening Tobacco cDNA Library. A partial castor (*Ricinus Communis* L.) cDNA clone (pCRS706) that encodes an amino acid sequence with 75% similarity and 57% identity to the biotin carboxylase subunit of Anabaena ACCase was identified by partially sequencing cDNA clones selected from a developing castor seed cDNA library by differential screening (van de Loo, F. T. et al., *Plant Physiol.* 108:1141–1150 (1995)). The coding region of the castor cDNA was amplified by PCR using synthetic primers and then used as a probe to screen a tobacco cDNA library by the plaque hybridization method using GeneScreenPlus membranes as described (Shorrosh, B. S. et al., *PNAS (USA)* 88:10941–10945 (1991)). The cDNA library was prepared in Lambda ZAPII (Stratagene) from poly (A)$^+$ RNA isolated from three- day old NT1 tobacco (*Nicotiana tabacum* L. cv bright yellow 2) cells. Prehybridization was at 42° C. for 4 h in solution A (5× SSC, 1% (w/v) SDS, 5× Denhardt's solution, 30% (w/v) formamide, 100 μg/mL ssDNA, and 0.1 M K$_3$PO$_4$, pH 6.8). Hybridization was at 42° C. overnight in solution A containing denatured labeled probe and 10% (w/v) dextran sulfate. Blots were washed twice in 2× SSC/1% SDS at room temperature and at 42° C. prior to autoradiography.

Plasmid Isolation and Sequencing. The pBluescript SK (−) vector containing the tobacco cDNA insert was in vivo excised from the Lambda ZAPII using the helper phage R408 as described (Stratagene). The rescued pBluescript phagemid containing the cloned insert was grown in *E. coli* XL1-Blue cells. Plasmids were prepared as described (Holmes, D. S. et al., *Anal. Biochem.* 114:193–197 (1981)) and the cDNA insert was sequenced on both strands using universal and synthetic primers and AmpliTaq DNA polymerase (BMB) with an ABI robotic catalyst and 373A DNA sequencer. Sequence alignments were determined by using the GAP program of Genetics Computer Group (University of Wisconsin, Madison).

Genomic DNA Isolation and Southern Blot Analysis. High molecular weight genomic DNA was isolated from the leaves of Arabidopsis, castor, tobacco, corn, rice, and wheat as described (Maniatis, T. et al., *Molecular Cloning: A Laboratory Handbook*, Cold Spring Harbor Laboratory Press, Cold Spring, N.Y., (1982)). The DNA (10 μg) was digested with EcoRV, HindIII, XbaI, or XhoI restriction endonucleases, resolved in an 0.7% (w/v) agarose gel, blotted to a GeneScreenPlus (NEN) nylon membrane, and hybridized at 55° C. in a solution containing denatured labeled probe generated by PCR using E3 cDNA clone primers JO288 and JO280 (FIG. 1), 1% (w/v) SDS, 50 mM Tris pH 7.6, 5× Denhardt's solution, 2.5 mM EDTA, 5× SSC, and 100 μg/mL denatured salmon sperm DNA (ssDNA). Prior to autoradiography, blots were washed at 55° C. for 20 min in 2× SSC/0.2% SDS, 1× SSC/0.2% SDS, and 0.5× SSC/0.2% SDS.

RNA Isolation and Northern Blot Analysis. Poly (A)$^+$ RNA was prepared from castor leaves and developing seeds using oligo- dT cellulose as described (Maniatis, T. et al., *Molecular Cloning: A Laboratory Handbook*, Cold Spring Harbor Laboratory Press, Cold Spring, N.Y., (1982)). mRNA (3 μg) was resolved in 1% agarose gel containing 2.2 M formaldehyde, was blotted onto nylon membrane (Hybond N, Amersham), and was fixed to the filter by exposure to UV light for 2 min. The blot was prehybridized at 42° C. for 4 h in a solution containing 5× SSC, 10× Denhardt's solution, 0.1% SDS, 0.1 M KPO$_4$, pH 6.8, and 100 μg/mL ssDNA. Subsequently, the blot was hybridized at 42° C. overnight in a solution containing denatured labeled probe, 5× SSC, 10× Denhardt's solution, 0.1 M KPO$_4$, pH 6.8, 100 μg/ml ssDNA, 10% dextran sulfate, and 30% formamide. The blot was washed twice in 2× SSC/0.5% SDS at room temperature and at 50° C. prior to autoradiography.

In Vitro Transcription and Translation. Based on the primary amino acid sequence of E3 (FIG. 1) and its alignment with Anabaena BC, it was hypothesized that the E3 cDNA encoded a chloroplastic protein of which the first 68 amino acids of its sequence represent a transit peptide (see Results). As a negative control for chloroplast uptake experiments, the cDNA sequence of E3 clone that encodes the suspected mature E3 protein, lacking the first 68 amino acids and replacing the Cys residue at position 69 with Met (FIG. 1), was amplified by PCR using primers JO288 (contains engineered Sac I and Nde I sites) and JO280 (contains engineered Xba I site) (FIG. 1). The amplified sequence was designated "−TE3" and was subcloned into the SacI/XbaI sites of pBluescript II KS (+). Both E3 and −TE3 clones were digested with Avr II (FIG. 1). Also, as a positive control, plasmid pCALACP (Savage, L. J. et al., *Plant Physiol.* 104:989–995 (1994)) containing the spinach ACP-I (spinach acyl carrier protein isoform I) was sequentially digested with EcoRI and BamHI. Subsequently, capped RNA transcripts were synthesized using 5 μg of the linearized clones and the MAXIscrip™ in vitro transcription kit (Ambion) as described by the manufacturer but with undiluted GTP (10 mM stock), 40 units of both RNAsin and RNA polymerases (Boehringer). After 1 h, an additional 40 units of polymerases were added and incubated for 1 h at 37° C. Linearized E3 and ACP-I cDNAs were transcribed with T3 RNA polymerase and linearized. −TE3 cDNA was transcribed with T7 RNA polymerase. The DNA template was digested with 20 units of RNase-Free DNase (Boehringer), and the RNA was precipitated sequentially at −20° C. in 3.75 M ammonium acetate/67% (v/v) ethanol and then in 56 mM Hepes-KOH, pH 7.0/67% (v/v) ethanol. The final RNA pellet was resuspended in 50 μL DEPC-water and 3 μL was checked for degradation on a 6% polyacrylamide urea sequencing gel. The RNA (3 μL) was diluted with 6 μL water, heated for 10 min at 70° C., stored on ice, and translated in rabbit reticulocyte lysate (Promega Corp.) in a total volume of 50μL at 30° C. for 2 h using L-[$^{35}$S]Met (1200 Ci mmol$^{-1}$) (NEN) and 40 units of RNAsin (Boehringer).

Isolation of Plastids from Leaves and Seeds. Chloroplasts were isolated from pea (*Pisum sativum* cv little marvel (Burpee)) shoots and alfalfa (*Medicago sativa* L. cv Apollo) shoots (grown hydroponically) by using a Percoll gradient as described (Cline, K. et al., *J. Biol Chem.* 260:3691–3695 (1985)). Chloroplasts were resuspended in 1 mL import buffer (330 mM sorbitol/50 mM Hepes-KOH, pH 7.8). Resuspended pea chloroplasts (500 µL) were fractionated into soluble and insoluble fractions by freeze-thawing in liquid nitrogen 3 times (with vortexing), and then centrifugation at 14000×g. The pellet was resuspended in 500 µL import buffer. Plastids were isolated from castor endosperm as described (Miernyk, J. A., *Methods of Plant Analysis* pp. 259–295 Edited by H F Linskens and J. F. Jackson. Springer-Verlag Berlin Heidelberg (1985)). The final pellet was resuspended in 30 µL of import buffer and then pelleted through 10 and 20% (v/v) Percoll cushions as described (Borchert, S. et al., *FEBS Letters* 253:183–186 (1989)). Protein content was determined by the Bradford assay (Bradford, M. M.,*Anal. Biochem.* 72:248–254 (1976)) using BSA as a standard.

Chloroplast Uptake Reactions. Pea chloroplasts were isolated from 11-to 13-day old pea shoots using Percoll gradient as described (Cline, K. et al., *J. Biol. Chem.* 260:3691–3695 (1985)). The import reaction, 200 µL total volume, was carried out at 27° C. for 30 min and contained 10 mM Met, 3 mM Mg-ATP, 40 µL translation reaction (see above), 0.5 µg/µL chlorophyll, and import buffer (350 mM sorbitol/50 mM Hepes-KOH, pH 7.8). The reaction was terminated with 0.2 mg/ml thermolysin for 30 min on ice. Proteolysis was stopped with 10 mM EDTA and the intact chloroplasts were recovered by centrifugation in an eppendorf tube at 4,200×g for 6 min through 1 mL of 40% (v/v) Percoll cushion made in import buffer and 5 mM EDTA. The pellet was resuspended in 1 mL of import buffer/5 mM EDTA and pelleted at 3,000×g for 3 min. The pellet was resuspended in 80 µL of 1 mM $MgCl_2$/10 mM Hepes-KOH, pH 7.8, freeze-thawed in liquid nitrogen 3 times, and centrifuged at 15,000×g for 15 min. The supernatant was boiled in SDS sample buffer and separated in 15% (w/v) SDS-PAGE. The gel was fixed in 10% (v/v) acetic acid/ 40% (v/v) ethanol, vacuum dried, and exposed to X-ray film (Kodak XAR) for 3 to 6 days.

Production of Antiserum. The cDNA region of the castor pCRS706 clone encoding 124 amino acids was amplified by PCR to include NdeI (encodes the initiator Met) and BamHI sites at the 5' and the 3' ends of the amplified cDNA. The amplified cDNA was subcloned into the NdeII/BamHI sites of the pET15b expression vector and then used to transform BL21 (DE3) cells (Novagen). Subsequently, the castor E3-like protein was induced in BL21 (DE3) cells with 1 mM isopropyl-beta-D-thiogalacto-pyranoside dioxane free and then purified by the pET His-Tag system (Novagen). The purified protein was dialyzed against PBS (135 mM NaCl, 2.7 mM KCl, 4.3 mM $Na_2HPO_4$, 1.4 mM $KH_2PO_4$) buffer, and antiserum was obtained by immunizing a female New Zealand White rabbit.

Immunoblot analysis. For immunoblot analysis, proteins were extracted as follows: Alfalfa leaf proteins were extracted in solution B (100 mM MES, pH 6.5, 2 mM DTT, 0.4 MM PMSF, and 5 µg/mL of antipain, pepstatin, leupeptin, ∈-aminocaproic acid, and aprotinin). Percoll gradient- purified alfalfa and pea plastids were resuspended in import buffer (330 mM sorbitol/50 mM Hepes-KOH, pH 7.8). Castor plastids, pelleted through 10% and 20% (v/v) Percoll cushions, were resuspended in 50 mM Tris, pH 8.0, and 150 mM NaCl. Castor endosperm proteins were extracted in 50 mM Tris, pH 6.5, and 1 mM EDTA. Protein solutions were mixed with SDS-sample buffer, resolved by SDS-PAGE, and then transferred to nitrocellulose, using the Pharmacia Novablot system, in 25 mM Tris (pH 8.3), 192 mM Gly, 20% (v/v) methanol. Transferred protein was reversibly stained with Ponceau S and blocked in TBS (10 mM Tris, 0.9% (w/v) NaCl) containing 2.5% (w/v) BSA. Blotted protein was detected with either preimmune or immune serum (1:500) in TBST (TBS containing 0.05% (v/v) Tween 20) containing 1% (w/v) BSA, and visualized with alkaline phosphatase-conjugated anti-(rabbit immunoglobulin G).

Results

Library Screening and Sequence Analysis. cDNA clones were selected from a developing castor seed cDNA library by differential screening with developing-seed and leaf total cDNA probes. Clones expressed at low levels in leaves and low or moderate levels in developing seeds, were partially sequenced (van de Loo, F. T. et al., *Plant Physiol.* 108:1141–1150 (1995)). cDNA clone pCRS706 was found to encode a protein with 75% sequence similarity and 57% identity with the Anabaena biotin carboxylase subunit of ACCase (Gornicki, P. et al., *J. Bacteriology* 175:5268–5272 (1993)). To obtain a full-length tobacco cDNA clone, a $^{32}$P-labeled coding region of the castor cDNA was used as a probe to screen a tobacco cDNA library, constructed from mRNA isolated from three-day old NT1 tobacco cells. Out of 200,000 plaques screened, 7 positives were identified, and the cDNA insert was recovered in pBluescript SK (−). All positive cDNAs were partially sequenced at their 5' and 3' ends and were found to be identical. The longest cDNA insert (1957 bp) in clone E3 was subjected to full-length sequence analysis in both strands. The 5' untranslated region (84 bp) contains a stop codon in frame with the initiator Met. The 3' untranslated region (265 bp) contains two putative polyadenylation signals ATATAA and TTAAAT starting at positions 1107 and 1908, respectively. In FIG. 1, the 5' and 3' untranslated nucleotide regions are indicated by lower case letters. Also in FIG. 1, the location of primers JO288 and JO280 used to prepare probes and subclones is shown and the AvrII restrictions site used to generate truncated transcripts is indicated. Early poly adenylation after position 1894 (see FIG. 1) was identified in some clones.

As shown in FIG. 1, E3 encodes an open reading frame of 536 amino acids with a calculated molecular weight of 58394 and a pI of 6.69. The first 68 amino acids of E3 encoded protein (lower case letters in FIG. 1) do not align with Anabaena BC and are rich in Ser, Thr, Arg, and hydrophobic amino acids, which is characteristic of chloroplast transit peptides. The E3-encoded protein shares high sequence similarity with prokaryotic biotin carboxylases and other carboxylases. The E3 encoded protein contains a putative ATP binding motif (amino acid residues 219 to 240 (see FIG. 1)), similar to that of other carboxylases. The putative polyadenylation signal in the nucleotide sequence and a putative ATP-binding site in the amino acid sequence are underlined in FIG. 1. As observed for other prokaryotic biotin carboxylase subunits of ACCase, the E3-encoded protein lacks a biotin binding motif (MKM or MKL) which, however, is present in other carboxylases not associated with ACCase.

Chloroplast Uptake Experiment. In order to confirm that the N-terminal region of the E3 protein could serve as a chloroplast targeting sequence, chloroplast uptake experiments were performed. Three in vitro translated proteins E3-274 (truncated tobacco E3 protein encoding the first 274 amino acids), −TE3-274 (E3-274 protein lacking the first 68 amino acids), and ACP-I (spinach acyl carrier protein isoform I) were tested for uptake by pea or spinach chloroplasts. E3-274 (29 kDa) is a truncated E3 protein encoding the first 274 amino acids. As a negative control, −TE3-274 (22 kDa) was constructed as a further truncated E3-274 protein that lacks the 68-amino acid putative transit peptide and replaces the Cys residue at position 69 with an initiator Met. A truncated form of E3 protein for chloroplast import was used for the following two reasons: first, the translated full-length E3 protein (about 58 kDa) and the suspected mature −TE3 protein (E3 protein lacking the first 68 amino acids (about 51 kDa)) in SDS-PAGE were obscured by the high levels of Rubisco protein which ran at 50 to 55 kDa on SDS-PAGE, and second, some endogenous chloroplast protein was radiolabeled in the uptake experiment even in the presence of excess unlabeled Met (see Materials and Methods). These radiolabeled chloroplast proteins had similar mobility to the suspected mature −TE3 protein and thus complicated interpretation of the data. Use of truncated forms of E3 protein (E3-274 and −TE3-274) simplified data interpretation because their mobility was not obscured by Rubisco or the endogenously radiolabeled chloroplast proteins. Also, because E3-274 and −TE3-274 transcripts were smaller than E3, the efficiency of in vitro transcription and translation increased. Spinach ACP-1, whose uptake into chloroplasts has been well-characterized, was used as a positive control for the uptake experiments.

In FIG. 2, in vitro translated E3-274, −TE3-274 and ACP-I proteins were loaded in the specified "T" lanes. Imported E3-274, −TE3-274, and ACP-I proteins were loaded in the specified "I" lanes. The molecular weight markers in FIG. 2 are indicated in kDa. The apparent molecular weights of E3-274, −TE3-274, and ACP-I translated proteins by SDS-PAGE analysis are 30, 23, and 20 kDa, respectively (see FIG. 2, lanes 1, 3 and 5). The presence of a second translation product for −TE3-274 with an apparent molecular weight of 19 kDa is probably due to initiation of translation at the next Met residue at position 93 (see FIG. 1). The import of E3-274 and ACP-I translated proteins into pea or spinach chloroplasts was verified by the presence of proteins with apparent molecular weights of 22 and 14 kDa, respectively (FIG. 2, lanes 2 and 6). In contrast, −TE3-274 translated protein was not taken up by pea or spinach chloroplasts, as indicated by the absence of radiolabeled protein from the isolated chloroplasts (see FIG. 2, lane 4). The processed E3-274 protein was slightly smaller than −TE3-274 protein, suggesting that E3 protein may contain a transit peptide that is longer than the first 68 amino acids in E3 protein.

Figure 3:
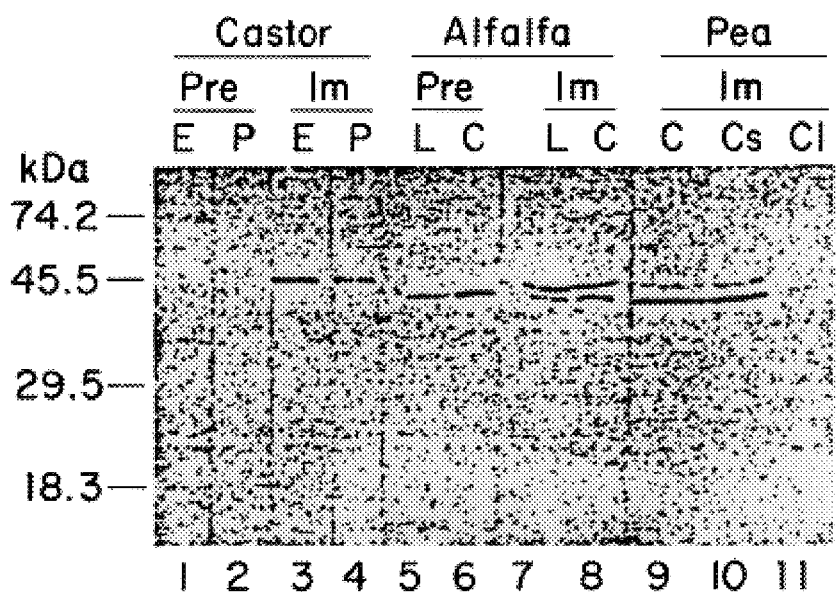
FIG. 3 is a photograph of a Western blot showing the results of an immuno blot analysis of the protein of the present invention in various plants.

Immuno Blot Analysis and Subcellular localization of E3 Protein in Different Plants. Antibodies were raised to the 124 amino acids encoded by the C-terminal region of the putative biotin carboxylase cDNA from castor. Proteins isolated from alfalfa, pea, and castor were analyzed by immunoblots using pre-immune and immune sera (see FIG. 3). More specifically, protein was resolved by 15% (w/v) SDS-PAGE and then transferred to a nitrocellulose membrane. Blots were treated with either E3 preimmune serum (pre) or with E3 immune serum (Im) as indicated in FIG. 3. Castor protein (100 μg) was isolated from the endosperm (E) and plastids (P). Alfalfa protein (100 μg) was isolated from leaves (L) and chloroplasts (C). Pea protein (100 μg) was isolated from chloroplasts (c) and fractionated into soluble (Cs) and insoluble (Ci) fractions. In FIG. 3, molecular weight markers are indicated in kDa.

As shown in FIG. 3, both the pre-immune and immune sera detected a protein band with molecular weight of about 40 kDa in the pea (lanes 9, 10 and 11) and alfalfa (lanes 5, 6, 7 and 8) leaves and chloroplasts. In addition to the 40 kDa protein band, immune serum detected a stronger band of about 47 kDa in the pea chloroplasts (lane 9) and alfalfa leaves (lane 8). The mobility of the 47 kDa protein band appears to be distorted by the high level of Rubisco protein, which migrates at about 50 to 55 kDa. When pea chloroplasts were fractionated by freeze-thawing, the 47 kDa protein was detected in the soluble fraction (lane 10) and was absent from the insoluble fraction (lane 11). The pre-immune serum detected a protein band with molecular mass of about 53 kDa in the plastids of castor seeds (lane 2) but not in the endosperm (lane 1). This is probably because the 53-kDa protein is at higher concentration in the plastid preparation than in the total endosperm protein extract. The immune serum detected a protein band with molecular weight of about 50 kDa in castor seeds both in the endosperm (lane 3) and the plastids (lane 4) and only detected the 53 kDa protein in the plastids (lane 4). Thus E3-like protein has an apparent molecular weight of about 47 kDa in the chloroplasts of pea and alfalfa leaves (due to its distorted mobility) and about 50 kDa in the plastids of castor seeds. The encoded E3 protein has a calculated molecular weight of about 58 kDa and the chloroplast uptake experiment (see above) suggested that E3 has a transit peptide with molecular weight of about 8 kDa. Thus the expected mature E3 protein is about 50 kDa, which coincides with the apparent molecular weight of E3 in the plastids of castor seeds as determined by immunoblot analysis (see FIG. 3).

Figure 4:
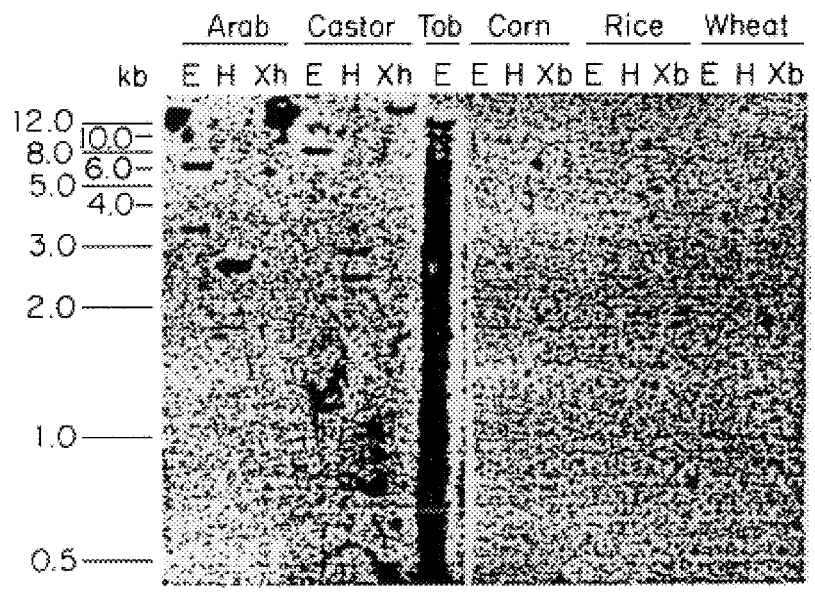
FIG. 4 is a photograph of a blot showing the results of the genomic organization and expression analysis of the gene of the present invention.

Genomic Organization and Expression of E3. Genomic DNA digested with restriction endonucleases was analyzed by probing southern blots with tobacco E3 coding region at moderate hybridization stringency and washing conditions. More specifically, high molecular weight genomic DNA isolated from Arabidopsis (Arab), castor, tobacco (Tob), corn, rice and wheat (10 μg) was digested with EcoRV (E), HindII (H), XbaI (Xb), or XhoI (Xh) restriction endonucleases, resolved in an 0.7% (w/v) agarose gel, blotted to nylon membrane, and hybridized at 55° C. in an aqueous solution with tobacco E3 cDNA probe. In FIG. 4, molecular weight markers are indicated in kb. The blot of FIG. 4 was exposed to X-ray film overnight. However, exposure of the blot to X-ray film for 7 days did not show any hybridization bands in the Gramineae lanes.

Figure 6A:
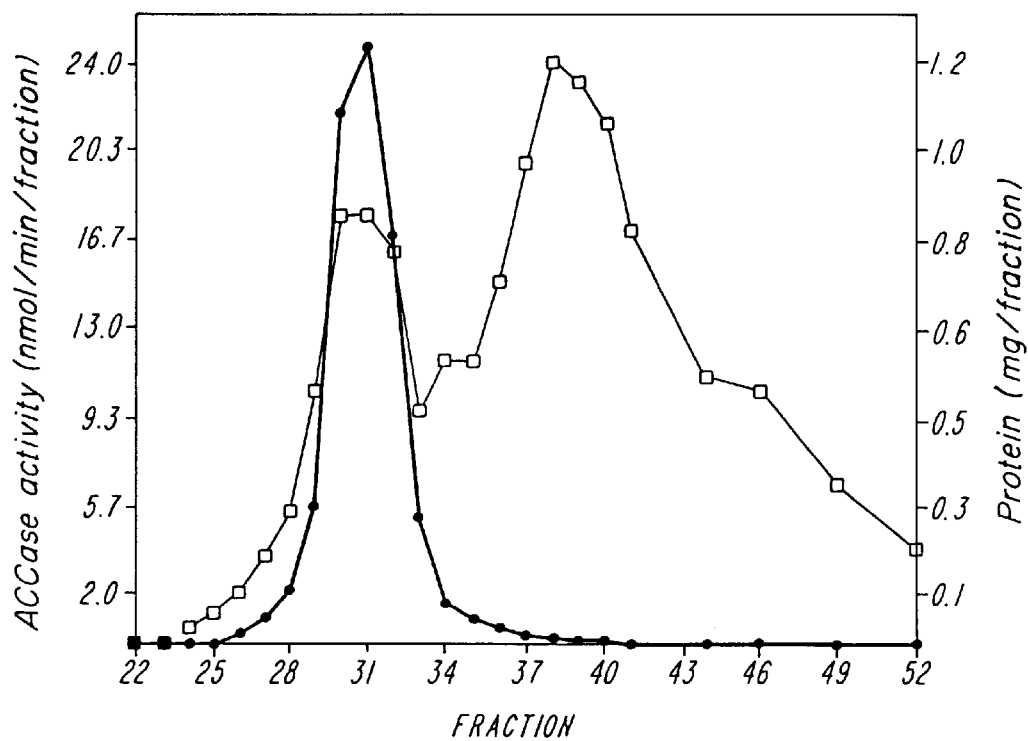
FIGS. 6A and 6B are a graph and photograph of a gel, respectively, showing the fractionation of pea chloroplast proteins by gel permeation chromatography.
Figure 6B:
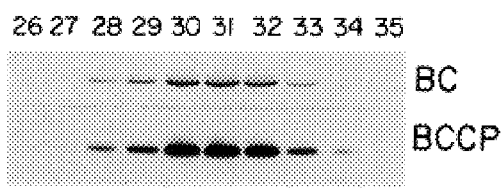

The probe detected approximately one gene in Arabidopsis, two genes in castor, and three to four genes in tobacco. In contrast, under these conditions, the probe did not hybridize to genomic DNA isolated from corn, rice, or wheat (see FIG. 4). These results support the suggestion of Konishi, T. et al., *PNAS (USA)* 91:3598–3601 (1994) that the heteromeric ACCase does not occur in plastids of Gramineae. However, the absence of cross-hybridization could indicate that E3-like DNA in the Gramineae is sufficiently different that it does not cross-hybridize with the tobacco E3 cDNA. The castor E3-like cDNA probe was used in Northern blot analysis of poly (A) RNA isolated from developing seeds and leaves of castor plants. Poly (A)$^+$RNA (3 μg) was prepared from castor leaves (L) and developing seeds (S), resolved in 1% (w/v) agarose gel containing 2.2 M formaldehyde, blotted to nylon membrane, and hybridized at 42° C. in 30% formamide solution with castor E3-like (E3) cDNA probe (A) or with β-tubulin 2 (TUB2) gene from *Colletrichum graminicola* (Panaccione and Hanau, 1990) (B). As shown in FIGS. 6A and 6B, molecular weight markers are indicated in kb. Blot "A" was exposed to X-ray film for 2 h. No other bands appeared with longer exposure.

Figure 5A:
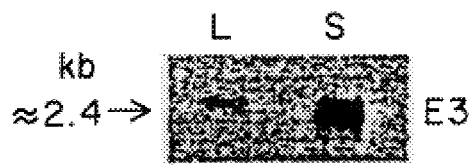
FIGS. 5A and 5B are photographs of Northern blots showing the results of an analysis of the tissue-specific expression of the gene of the present invention.
Figure 5B:
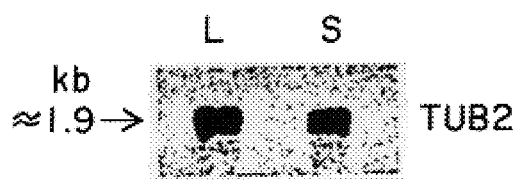

As shown in FIGS. 5A and 5B, a single hybridizing band of about 2.4 kb was detected in both developing seed and leaf tissue. Expression of E3-related sequences was approximately 10 times higher in the seeds than in the leaves (see FIG. 5A). As a control for RNA loading, the same blot was re-probed with β-tubulin 2 gene from *Colletotrichum graminicola* and approximately the same expression level of this constitutive gene was observed in seeds and leaves (see FIG. 5B).

The following Specific Example describes studies performed to further characterize the gene of the present invention.

SPECIFIC EXAMPLE 2

Materials and Methods

ACCase activity assays. ACCase activity was measured as acid stable incorporation of radioactivity from Na $H^{14}CO_3$, in an assay modified from Sauer and Heise (Sauer and Heise, *Z. Naturforsch* 39c:268–275 (1984)) and Alban et al. (Alban et al., *Biochem J.* 300:557–565 (1994)). The assay consisted of 100 mM Tricine, pH 8.2,100 mM KCL, 2.5 mM $MgCl_2$, 0.5 mM acetyl-CoA, 1 mM ATP, 10 mM $NaH^{14}CO_3$ (1 mCi/mmol) and enzyme sample in a total volume of either 50 μL or 100 μL. Assays were started with addition of enzyme and incubated at 30° C. for 15 min. Assays were stopped with 100μL of 2N HCl, and 150 μL total volume was transferred to a scintillation vial, dried and counted by liquid scintillation. Duplicate assays and minus acetyl-CoA controls were included.

Immunoblots. For BC immunoblots, rabbit antibodies to the C-terminal 124-amino acid region of the recombinant castor BC were used at a 1:500 dilution. The secondary antibody was a 1:2000 dilution of alkaline phosphatase-conjugated anti-rabbit IgG from Kirkegaard and Perry, Gaithersburg, Md., USA. For determination of biotinylated polypeptides, a 1:2000 dilution of anti-biotin IgG conjugated to alkaline phosphatase (Sigma) was used except for the castor development blot, which was probed with ExtrAvidin-alkaline phosphatase (Sigma, St. Louis, Mo., USA) at a 1:5000 dilution. Protein was electrotransferred at 100 milliamps overnight using a model TE-42 Transphor wet blot apparatus from Hoefer, San Francisco, Calif., USA. For increased sensitivity, anti-biotin immunoblots to detect the MF ACCase in rapeseed or castor were developed with the Lumi-Phos 530 chemiluminescent substrate according to the directions of the manufacturer, Boehringer, Mannheim, Indianapolis, Ind., USA. The extraction buffer as 50 mM HEPES, pH 8.0, 1 mM EDTA, 1 mM DTT, 1 mM PMSF, 1 mM benzamidine hydrochloride and 5 mM ε-amino-n-caproic acid. All plant samples were solubilized with a plastic pestle in a microfuge tube, except for the castor leaf and root samples which were ground in liquid nitrogen. Protein concentrations were determined by the method of Bradford (Bradford, M. M., *Anal. Biochem.* 72:248–254 (1976)) using bovine gamma globulin as standard.

Castor seed development. Developing castor seed was staged according to Greenwood and Bewley (Greenwood and Bewley, *Can. J. Bot.* 60:1751–1760 (1982)). Endosperm was then halved, and fresh weight was determined for each half. One half, A, was frozen in liquid nitrogen for later activity assays and immunoblots. The other half, B, was lyophilized and dry weight was determined. Half B was then minced with razor blade and fatty acid methyl esters were prepared by heating the tissue at 90° C. for one hour in 10% (wt/vol) boron trichloride/methanol (Sigma) supplemented with 30% toluene (vol/vol). Fatty acid methyl esters were extracted with hexane, dried, and weighed. Half A was solubilized in 10 μL of buffer per mg calculated dry weight, using the same extraction buffer reported for immunoblot methods, except that 10% glycerol was also included. Following centrifugation at 10,000 g for 5 min, ACCase activity of the supernatant minus fat pad was determined, using 10 μL endosperm extract (from 1 mg dry weight). For immunoblots, protein extracted from 1.5 mg dry endosperm weight was blotted.

Fractionation of pea chloroplast proteins by gel permeation chromatography. This method was similar to that of Alban et al. (Alban et al., *Biochem J.* 300:557–565 (1994)). Chloroplasts were isolated from 70 to 130 g of 12-day old pea seedlings by the method of Roughan (Roughan, G., *Meth. Enz.* 148:327–337 (1987)). Chloroplasts were lysed in the following lysis buffer: 50 mM HEPES, pH 8.0, 0.1% Triton X-100, 10% glycerol, 1 mM EDTA, 1 mM DTT, 1 mM PMSF, 1 mM benzamidine hydrochloride and 5 mM ε-amino-n-caproic acid. After centrifugation at 37,000 g for 30 min, the stromal fraction (about 20 mg total protein) was collected and loaded onto a HiPrep 16/60 Sephacryl S-300 HR column (Pharmacia, Uppsala, Sweden) equilibrated with lysis buffer minus Triton X-100. Three-ml fractions were collected and used for ACCase activity assays and immunoblots. Although antibodies were raised against a BC peptide of castor, pea chloroplasts were used for gel permeation chromatography because the pea chloroplast enzyme was found to be more stable during purification than the castor plastid enzyme.

Immunoprecipitation byanti-biotin carboxylase antibodies. IgG fractions were prepared from immune and pre-immune sera by DEAE-cellulose chromatography. Pea chloroplast ACCase partially purified by gel permeation chromatography was incubated with immune or pre-immune IgG for one hour on ice. IgG-sorb (The Enzyme Center, Malden, Mass., USA) that had been preincubated with 0.5 mg/ml BSA was added to precipitate antigen-antibody complexes. Following a 15 min incubation on ice and centrifugation at 14,000 g for 2 min, the supernatant was assayed from ACCase activity. The pellets were boiled in SDS loading buffer (Laemmli, U. K., *Nature* 227:680–685 (1970)), electrophoresed by SDS-PAGE, and blotted as described above.

*Brassica napus* staging. At each stage, embryos from an entire silique were removed from seed coats, and several were pooled and solubilized from immunoblots as described above. The remainder were pooled, minced with a razor blade and lyophilized, and fatty acid methyl esters were prepared as described for the castor staging experiment, and then analyzed by gas chromatography.

Preparation of acyl-ACPs. Acyl-ACPs were synthesized from radioactive fatty acids and recombinant spinach ACP-I (Beremand et al., *Arch. Bioch. Biophys.* 256:90–100 (1987)) (ca. 50% pure following expression of *E. coli*) using the *E. coli* acyl-ACP synthetase method of Rock and Garwin (Rock and Garwin, *J. Biol. Chem.* 254:7123–7128 (1979)). Acyl-ACPs were purified by DEAD-cellulose chromatography.

Results

The BC protein co-purifies with ACCase activity and with BCCP. Pea chloroplast proteins were fractionated on a Sephacryl S-300 HR gel permeation column, and the fractions were assayed for the ACCase activity. In FIG. 6A, ACCase activity (•---•) and protein (□--□) of fractions eluted from a Sephacryl S-300 HR column is shown. ACCase specific activity was enriched approximately 10-fold, with >80% recovery of activity from the gel permeation column. Immunoblots of the column fractions were also prepared and probed with antibodies to castor putative BC (C-terminal 124-amino acid region) or with antibodies to biotin (see FIG. 6B). A single biotinylated polypeptide of 38 kDa was observed, consistent with previous reports of a single 35 to 38-kDa biotinylated polypeptide from pea chloroplasts that is considered to be the BCCP subunit of ACCase (Sasaki et al., *J. Biol. Chem.* 268:25118–25123 (1993); and Alban et al., *Biochem J.* 300:557–565 (1994)). A 52-kDa putative BC polypeptide was detected by antibodies raised to the castor peptide, consistent with the size predicted from the full-length tobacco cDNA. The 52-kDa putative BC polypeptide co-eluted exactly with ACCase activity and with the biotinylated polypeptide.

Figure 7B:
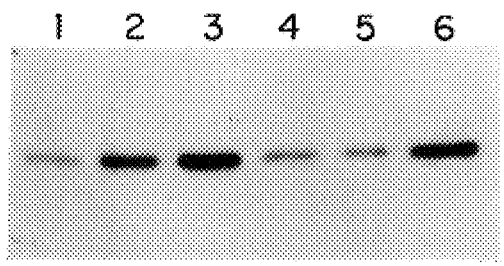
FIGS. 7A and 7B are a graph and photograph of a blot, respectively, showing the immunoprecipitation of pea chloroplast proteins by antibodies to castor BC.
Figure 7A:
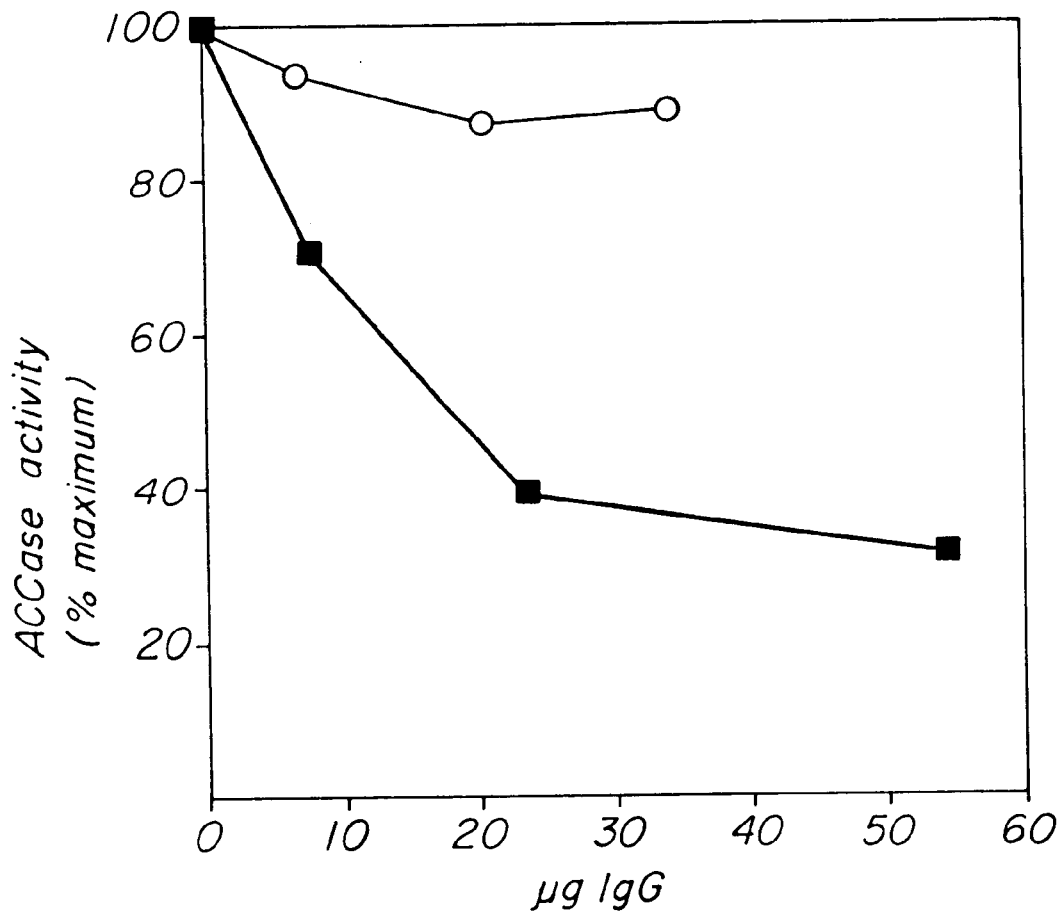

Antibodies to BC co-immunoprecipitate ACCase activity and BCCP. As further confirmation that the two polypeptides shown in FIGS. 6A and 6B were part of the same protein complex, and were not just co-purifying by chance, immunoprecipitation experiments were conducted with the gel permeation purified protein of FIGS. 6A and 6B. Immune castor BC sera, but not pre-immune sera, precipitated and/or inhibited ACCase activity. In FIG. 7A, precipitation and/or inhibition of ACCase activity (from fraction #29 of FIGS. 6A and 6B) by BC immune sera (■--■) or pre-immune sera (○--○) is shown. The immunoprecipitated protein pellet was solubilized, fractionated by SDS-PAGE, and used in an immunoblot probed with antibodies to biotin. In FIG. 7B, anti-biotin immunoblot of immunoprecipitated proteins from 3A, following fractionation by SDS-PAGE is shown. Lanes 1 to 3 were the three immunoprecipitates resulting from 5, 22, and 52 µg of BC immune IgG. Lanes 4 and 5 were immunoprecipitates resulting from 5 to 20 µg of pre-immune IgG. Lane 6 was a control aliquot from fraction #29 of FIGS. 6A and 6B, not immunoprecipitated. The degree of precipitation of ACCase activity was correlated with the amount of the 38-kDa biotinylated polypeptide detected in the pellet. Thus, the antibodies to BC co-immunoprecipitated BCCP.

Figure 8:
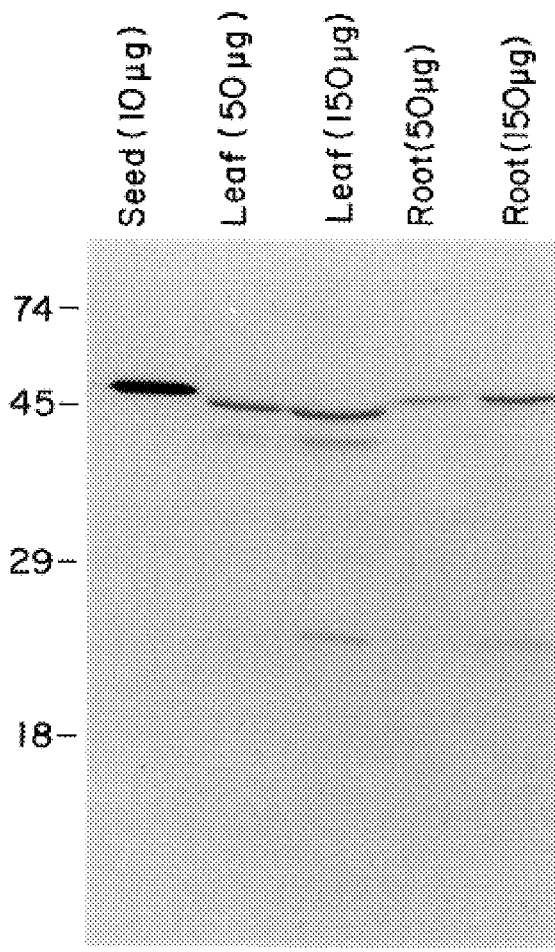
FIG. 8 is a photograph of a blot showing protein extracts from castor tissues probed with antibodies of the castor putative BC.

The BC polypeptide is more abundant in a developing oilseed than in leaf or root. If the putative BC polypeptide is a subunit of an ACCase involved in fatty acid synthesis, then greater quantities of the polypeptide may be expected in tissues undergoing high rates of fatty acid synthesis, such as a developing oilseed. To further confirm this, an immunoblot of protein extracts from various castor tissues was probed with antibodies to the putative BC from castor seed endosperm. As shown in FIG. 8, the indicated quantities of protein from seed endosperm (approximately stage V.5 according to Greenwood and Bewley, *Can. J. Bot.* 60:1751–1760 (1982)), young expanding leaf (6 cm at widest point), or root of a soil grown young seedling (with unifoliates plus 4 true leaves) were blotted. In FIG. 8, molecular masses in kDa are given on the left. A 50-kDa polypeptide was detected in castor endosperm and root. The corresponding leaf polypeptide appeared to be slightly smaller, probably due to distortion by large quantities of the rubisco large subunit. More of the putative BC polypeptide was evidence in 10 µg of endosperm protein than in 150 µg of leaf or root protein, assuming no large antigenic differences between the BC from these tissues. BC comprised approximately 0.8% of the total soluble protein in castor endosperm, as estimated by immunoblots using several concentrations of the purified recombinant castor BC as standard. BC therefore comprised 0.05% of less of the protein in leaf and root.

Figure 9:
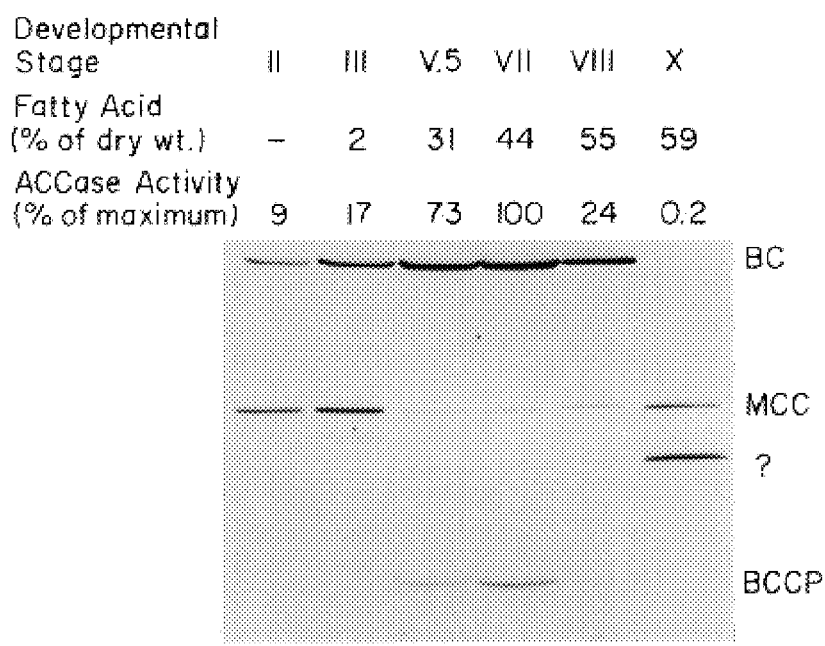
FIG. 9 is a photograph of a blot showing the ACCase developmental expression in castor seed endosperm.

Expression of BC, BCCP, and ACCase activity is coordinated during castor seed development. Castor seed has one of the highest seed oil contents known, at about 60% of dry weight, and it therefore seemed to be an attractive tissue with which to examine ACCase developmental expression. Developing castor seed was staged according to published procedure (Greenwood and Bewley, *Can. J. Bot.* 60:1751–1760 (1982)) and according to fatty acid content. For each developmental stage, ACCase activity was determined (see FIG. 9). Immunoblots of protein extracts from 1.5 mg endosperm dry weight for each stage were probed with castor BC antibodies or with avidin to identify biotinylated polypeptides. Three biotinylated polypeptides were observed, in contrast to the single polypeptide observed in pea chloroplasts. The three biotinylated polypeptides had apparent molecular masses of approximately 76, 48 and 29 kDa. ACCase specific activity at stage VII was 0.69 nmol min$^{-1}$ (mg dry weight)$^{-1}$ or 7.43 nmol min$^{-1}$ (mg protein)$^{-1}$.

Based on size, the 76-kDa polypeptide is probably the mitochondrial methylcrotonyl-CoA carboxylase (Baldet et al., *Plant Physiol.* 99:450455 (1992); and Song et al., *PNAS (USA)* 91:5779–5783 (1994)). The 48-kDa polypeptide had an apparent molecular mass different from that of any plant biotin-dependent carboxylase (Baldet et al., *Arch. Biochem. Biophys.* 303:67–73 (1993)), and it was most abundant in mature seed, a relatively inactive tissue metabolically. This castor polypeptide may be similar in function to the pea 65-kDa biotin storage polypeptide that was the major biotinylated polypeptide of mature seed, but was not associated with any biotin-dependent carboxylase activity (Duval et al., *Plant Mol Biol.* 26:265–273 (1994); and Duval et al., *Biochem J.* 299:141–150 (1994)). The 29-kDa biotinylated polypeptide appeared to be the only reasonable candidate for BCCP in this tissue. This polypeptide may actually be a proteolytic breakdown product of a 35 to 38-kDa polypeptide, as was observed previously with pea BCCP extracted from whole leaves rather than chloroplasts (Konishi and Sasaki, *PNAS (USA)* 91:3598–3601 (1994)). In other immunoblots with developing rapeseed and Crambe seed extracts, we observed several biotinylated polypeptides ranging in size from 38 to 28 kDa that may reflect breakdown of the 38-kDa BCCP. As evident in FIG. 9, ACCase activity, BC levels, and BCCP levels increased and subsequently decreased in parallel during development. In contrast, the abundance of the other biotinylated polypeptides was not correlated with ACCase activity. Another castor immunoblot was probed with antibodies to biotin and was then developed with a sensitive chemiluminescent method in an attempt to detect the 200-kDa MF ACCase. This polypeptide was not detected in this tissue.

Figure 10:
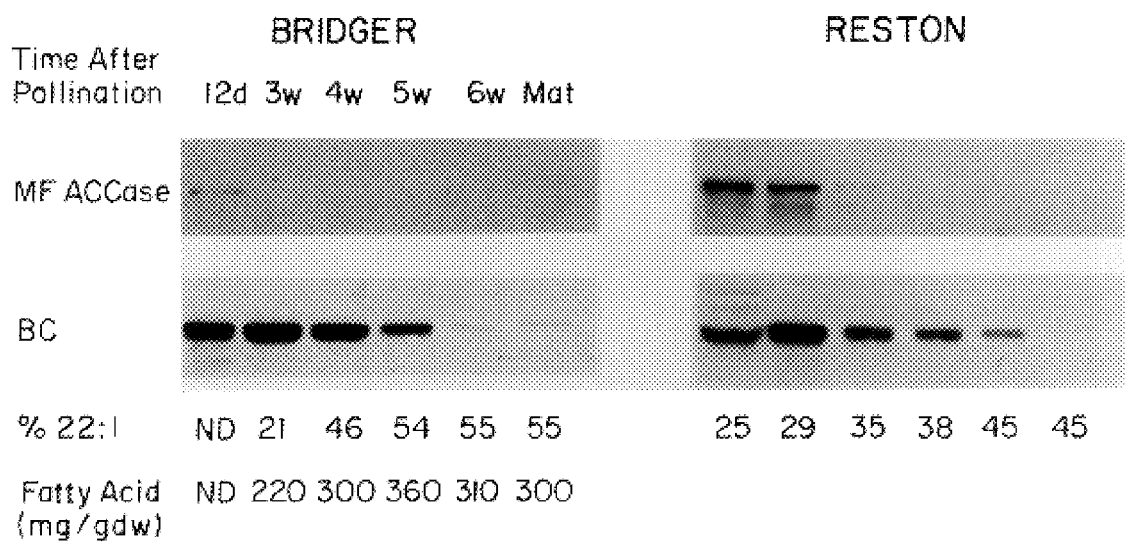
FIG. 10 is a photograph of a blot showing the developmental expression of rapeseed multi-functional ACCase and the BC subunit of the present invention.

The rapeseed MF and MS ACCases have different developmental expression patterns. Rapeseed oil has considerable quantities of the very long fatty acids gadoleic acid (20:1) and erucic acid (22:1). These very long chain fatty acids are synthesized outside the plastid by elongation of oleic acid exported from the plastid (Pollard and Stumpf, *Plant Physiol.* 66:649–655 (1980)). Malonyl-CoA is needed for the elongation reactions (Harwood, J. L., *Annu. Rev. Plant Physiol. Plant Mol. Biol.* 39:101–138 (1988)) and may be provided by an extra-plastidial ACCase. To explore this possibility, rapeseed embryos from two high erucic acid cultivars were staged according to time after pollination and/or the content of erucic acid, which is known to increase throughout development of rapeseed and mustard (Norton and Harris, *Planta.* 123:163–174 (1975); and Mukherjee and Kiewitt, *Phytochem.* 23:349–352 (1984)). The levels of BC and of the MF ACCase were determined by immunoblots (see FIG. 10). Five μg of protein per lane were used for BC immunoblots, and 50 μg or 20 μg were used for the anti-biotin blots in Reston or Bridger cultivar, respectively. Protein was extracted from embryos only, following removal of seed coats. Both MF and MS ACCase were detected in this tissue, unlike castor endosperms. The BC polypeptide was observed throughout embryo development, peaking at 3 weeks after pollination in Bridger cultivar, but was barely detectable in mature seed. In contrast, the MF ACCase was detected in early in embryo development in both cultivars. The erucic acid content in Bridger cultivar more than doubled between three and four weeks after pollination, at a time when total fatty acid content was also increasing, but the MF ACCase was not detected at those times. It thus appeared that fatty acid elongation was not well correlated with the MF ACCase levels.

Figure 11:
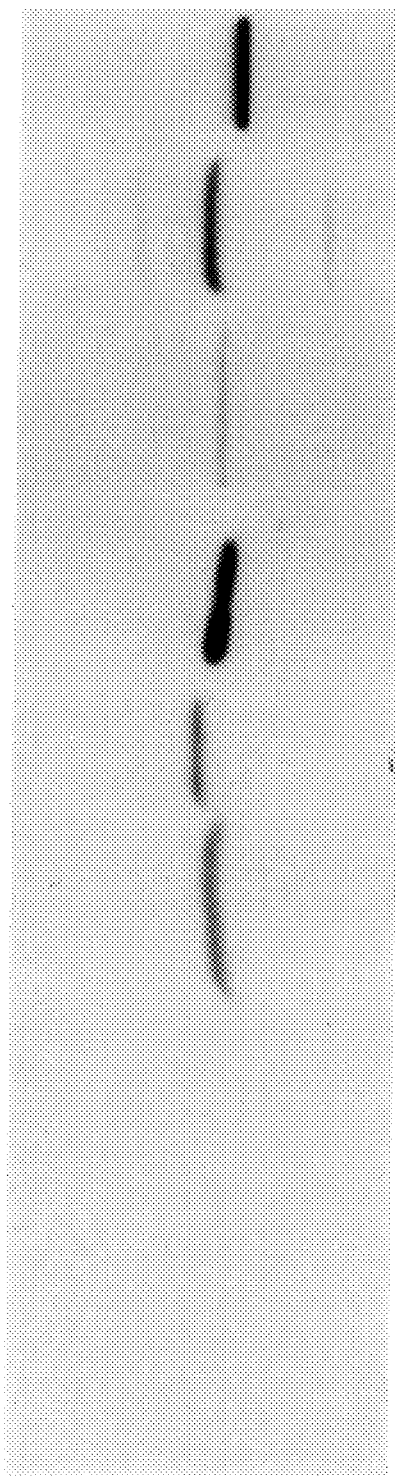
FIG. 11 is a photograph of a blot showing protein extracts from dicotyledons and monocotyledons probed with antibodies to castor BC.

BC is present in some monocotyledons. The MC ACCase was previously detected in dicotyledons, but not in the Gramineae (Konishi and Sasaki, *PNAS (USA)* 91:3598–3601 (1994)). To determine the presence or absence of the MS ACCase in other monocotyledons besides the Gramineae, immunoblots were probed with castor BC antibodies (see FIG. 11). Protein extracts were from developing seeds of Crambe, Iris, day lily, and switchgrass, or from nearly mature Crocus seed. Other extracts were from onion bulb, castor seed plastids, avocado mesocarp, and barley etiolated shoot. Five μg of protein for Crambe and castor, and 50 μg for other samples were used.

Polypeptides cross-reacting with the BC antibodies were detected in the dicotyledons castor, avocado, and Crambe, and in the monocotyledons day lily, Iris, and onion, but not in the Gramineae members barley and switchgrass. The BC polypeptide was also not detected in the non-Gramineae monocotyledon Crocus. However, the Crocus protein extract was from nearly mature seed, and in light of the immunoblots of FIGS. 9 and 10, BC may be detectable in Crocus seed at an earlier stage. The immunoblots of FIG. 11 suggest that BC, and therefore the MS form of ACCase, is present in some monocotyledons.

Metabolites of fatty acid synthesis do not significantly inhibit castor endosperm and pea chloroplast ACCase. The effects of metabolites of fatty acid synthesis on castor endosperm and/or pea chloroplast ACCase activity are presented in Table 1, below. The pea enzyme was partially purified by Sephacryl S-300 HR gel permeation chromatography. Recombinant spinach ACP-I was used for acyl-ACP synthesis. In Table 1, values are means of duplicate determinations ± standard deviation and values in parentheses are minus acyl-ACP controls, and represent effects of an equal volume of the buffer (10 mM MES, pH 6.1, 500 mM NaCl) used to elute acyl-ACPs from DEAE-cellulose during preparation.

As shown by the results set forth in Table 1, long-chain acyl-ACPs did not significantly inhibit the castor or pea enzymes, because activity was as high or higher in the presence of acyl-ACPs as in the minus acyl-ACP controls. Oleic acid of ACP at 10 μM concentrations of long chain acyl-ACPs and free fatty acids are probably <2 μM and that ACP concentrations are only 4 to 6 μM (Post-Beittenmiller et al., *J. Biol. Chem.* 266:1858–1865 (1991)), the results of Table 1 suggest that none of these metabolites have a major direct role in ACCase regulation in vivo.

TABLE 1

Effects Of Metabolites Of Fatty Acid Synthesis On Castor Endosperm Or Pea Chloroplast ACCase Activity

| Addition | Castor ACCase Activity (% of Control) | Pea ACCase Activity (% of control) |
|---|---|---|
| Control | 100 | 100 |
| 1 μM 16:0-ACP | — | 98 ± 2 (94) |
| 3 μM 16:0-ACP | — | 91 ± 4 (87) |
| 10 μM 16:0-ACP | 75 ± 3 (60) | 77 ± 4 (61) |
| 1 μM 18:1-ACP | — | 97 ± 1 (94) |
| 3 μM 18:1-ACP | — | 87 ± 3 (87) |
| 5 μM 18:1-ACP | 81 ± 9 (81) | — |
| 10 μM 18:1-ACP | 63 ± 11 (56) | 79 ± 14 (61) |
| 10 μM 16:0 | 97 ± 8 | — |
| 10 μM 18:1 | 72 ± 10 | — |
| 10 μM ACP | 88 ± 1 | 89 ± 5 |

DISCUSSION

A 50-kDa biotin carboxylase subunit of plant heteromeric ACCase is encoded by the gene of the present invention. Because there are many carboxylase enzymes in plants (such as methyl-crotonoyl-CoA carboxylase, propionyl-CoA carboxylase, etc.) which have similar amino acid sequences, the identification of the subject of this invention as a subunit of acetyl-CoA carboxylase (rather than a subunit of other carboxylases) could not be done based solely on nucleic acid or amino acid homology. The present application sets forth several lines of evidence documenting the conclusion that the sequence set forth herein is the biotin carboxylase subunit of ACCase.

The tobacco E3 protein has sequence identity with the prokaryotic biotin carboxylase subunit of ACCase, which ranges from 71 to 80% similarity and 52 to 65% identity. Tobacco E3-encoded protein and prokaryotic BCs do not have the biotin binding site MKM or MKL, in contrast to eukaryotic carboxylases such as pyruvate carboxylase, propionyl-CoA carboxylase, acetyl-CoA carboxylase, and methylcrotonyl-CoA carboxylase (where BC is part of BCCP). However, similar to all carboxylases, the E3-encoded protein contains a putative ATP binding motif. In vitro uptake experiments and localization by cell fractionation and immunoblot analysis indicate that E3 protein contains a cleavable transit peptide and the mature 50-kDa protein is localized in the chloroplast. Higher expression of E3 transcripts in castor seeds versus leaves corresponds to the higher level of fatty acid biosynthesis in the seeds. The hybridization of tobacco E3 cDNA to genomic DNA only from dicot plants corresponds to the occurrence of the CT subunit of heteromeric ACCase in the chloroplast genome of tobacco and pea, to its absence from wheat, and to its presence only in truncated form in rice. Preliminary data on size-fractionated castor endosperm and pea chloroplast proteins by Sephacryl S-300 gel permeation chromatography showed an exact co-elution of ACCase activity with E3 protein and with a biotin-containing protein with molecular weight of about 35 kDa. A 35 to 38-kDa biotin binding protein is the major if not the only biotin protein in pea plastids and has been implicated to be the biotin carboxyl carrier protein (BCCP) subunit of heteromeric ACCase in pea chloroplasts (Alban, C. et al., *Biochem. J.* 300:557–565 (1994) and Konishi, T. et al., *PNAS (USA)* 91:3598–3601 (1994)).

Specific Example 2 provides further biochemical, immunological, and physiological evidence demonstrating that the gene of the present invention encodes the biotin carboxylase subunit of plant ACCase. Antibodies to the recombinant castor putative BC recognized a higher plant polypeptide that was associated with ACCase activity and with BCCP during purification, during immunoprecipitation, and during castor seed development. Furthermore, this polypeptide was more abundant in developing oilseed than in leaf or root, and was absent in the Gramineae. These observations are all consistent with expectations for a BC subunit of plant ACCase.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

All references referred to herein are incorporated by reference.

We claim:

1. An isolated and purified nucleic acid encoding a biotin carboxylase subunit of plant acetyl-CoA carboxylase, comprising a nucleotide sequence that hybridizes to SEQ ID NO: 1 or the complement of SEQ ID NO: 1 under high stringency wash conditions of 0.1× SSC at 65° C.

2. The isolated and purified nucleic acid of claim 1, wherein the nucleotide sequence encodes the polypeptide of SEQ ID NO: 2.

3. An expression vector comprising a nucleotide sequence encoding the polypeptide of SEQ ID NO: 2 operatively-linked to a promoter functional in a host cell.

4. The expression vector of claim 3, wherein the nucleotide sequence is that of SEQ ID NO: 1.

5. A plant containing the expression vector of claim 4.

6. A seed containing the expression vector of claim 4.

* * * * *